(12) United States Patent
Seiberg et al.

(10) Patent No.: US 6,750,229 B2
(45) Date of Patent: *Jun. 15, 2004

(54) METHODS FOR TREATING SKIN PIGMENTATION

(75) Inventors: Miriam Seiberg, Princeton; Stanley S. Shapiro, Livingston, both of NJ (US)

(73) Assignee: Johnson & Johnson Consumer Companies, Inc., Skillman, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/361,429

(22) Filed: Jul. 27, 1999

(65) Prior Publication Data

US 2002/0065300 A1 May 30, 2002

Related U.S. Application Data

(63) Continuation-in-part of application No. 09/110,409, filed on Jul. 6, 1998.

(51) Int. Cl.⁷ .................... A61K 31/445; A61K 31/205
(52) U.S. Cl. .................... 514/317; 514/321; 514/555
(58) Field of Search .................. 514/317, 321, 514/555

(56) References Cited

U.S. PATENT DOCUMENTS

| | | | |
|---|---|---|---|
| 3,625,976 A | 12/1971 | Theimer | 549/289 |
| 3,755,560 A | 8/1973 | Dickert | 514/772.6 |
| 4,151,304 A | 4/1979 | Evans | 424/361 |
| 4,190,671 A | 2/1980 | Vanstone et al. | 514/548 |
| 4,219,569 A | 8/1980 | Glenn | 514/685 |
| 4,223,018 A | 9/1980 | Belle | 424/177 |
| 4,254,105 A | 3/1981 | Fukuda | 514/762 |
| 4,272,544 A | 6/1981 | Cella | 424/273 |
| 4,278,570 A | 7/1981 | Flom | 252/546 |
| 4,279,930 A | 7/1981 | Hall | 514/685 |
| 4,297,348 A | 10/1981 | Frazier | 514/27 |
| 4,331,692 A | 5/1982 | Drevici | 426/310 |
| 4,333,927 A | 6/1982 | Ofuchi | 424/238 |
| 4,368,187 A | 1/1983 | Flom | 424/81 |
| 4,370,315 A | 1/1983 | Greff | 424/94 |
| 4,382,960 A | 5/1983 | Flom | 424/358 |
| 4,386,067 A | 5/1983 | Guillon | 424/95 |
| 4,421,769 A | 12/1983 | Dixon et al. | 514/772 |
| 4,427,670 A | 1/1984 | Ofuchi | 424/241 |
| 4,437,895 A | 3/1984 | Koulbanis | 106/245 |
| 4,439,418 A | 3/1984 | Moller | 514/685 |
| 4,462,981 A | 7/1984 | Smith | 424/27 |
| 4,486,448 A | 12/1984 | Ser | 424/294 |
| 4,488,564 A | 12/1984 | Grollier | 132/7 |
| 4,515,778 A | 5/1985 | Kastell | 424/95 |
| 4,524,067 A | 6/1985 | Arichi | 514/33 |
| 4,537,782 A | 8/1985 | Millet | 514/774 |
| 4,550,035 A | 10/1985 | Smith | 427/398 |
| 4,578,267 A | 3/1986 | Salamone | 424/78 |
| 4,584,190 A | 4/1986 | Tejima | 424/59 |
| 4,604,281 A | 8/1986 | Deckner | 424/59 |
| 4,612,192 A | 9/1986 | Scheuffgen | 424/70 |
| 4,690,821 A | 9/1987 | Smith | 424/401 |
| 4,707,293 A | 11/1987 | Ferro | 252/174 |
| 4,760,096 A | 7/1988 | Sakai | 514/847 |
| 4,793,991 A | 12/1988 | Slimak | 424/64 |
| 4,824,662 A | 4/1989 | Hofmann | 424/61 |
| 4,834,076 A | 5/1989 | Millet | 601/154 |
| 4,847,267 A | 7/1989 | Deckner | 514/311 |
| 4,851,214 A | 7/1989 | Walters | 424/65 |
| 4,859,458 A | 8/1989 | Salamone | 424/70 |
| 4,867,964 A | 9/1989 | Forestier | 424/47 |
| 4,871,530 A | 10/1989 | Grollier | 424/47 |
| 4,885,169 A | 12/1989 | Gazzani | 514/8 |
| 4,895,839 A | 1/1990 | Bombardelli | 514/78 |
| 4,906,457 A * | 3/1990 | Ryan | 424/59 |
| 4,943,462 A | 7/1990 | Komerska | 428/42 |
| 4,960,588 A | 10/1990 | Hoshowski | 424/71 |
| 4,960,764 A | 10/1990 | Figueroa | 514/63 |
| 4,970,216 A | 11/1990 | Deckner | 514/311 |
| 5,002,761 A | 3/1991 | Mueller | 424/70 |
| 5,032,382 A | 7/1991 | Crollier | 424/47 |
| 5,032,400 A | 7/1991 | Wiersum | 424/195 |
| 5,043,323 A | 8/1991 | Bombardelli | 514/25 |
| 5,077,038 A | 12/1991 | Hofmann | 424/61 |
| 5,077,040 A | 12/1991 | Bergmann | 424/70 |
| 5,104,655 A | 4/1992 | Bombardelli | 424/195 |
| 5,110,603 A | 5/1992 | Rau | 424/466 |
| 5,116,605 A | 5/1992 | Alt | 424/70 |
| 5,118,671 A | 6/1992 | Bombardelli | 514/26 |
| 5,147,859 A | 9/1992 | Bombardelli | 514/26 |
| 5,166,139 A | 11/1992 | Bombardelli | 514/26 |
| 5,171,577 A | 12/1992 | Griat | 424/450 |
| 5,179,091 A | 1/1993 | Lesieur | 514/224.5 |
| 5,188,823 A | 2/1993 | Shapiro | 424/65 |
| 5,192,332 A | 3/1993 | Lang | 8/405 |
| 5,194,252 A | 3/1993 | Hofmann | 424/73 |
| 5,217,717 A * | 6/1993 | Kennedy et al. | 424/195.1 |
| 5,229,104 A | 7/1993 | Sottery | 424/59 |

(List continued on next page.)

FOREIGN PATENT DOCUMENTS

| | | |
|---|---|---|
| EP | 0421021 | 10/1989 |
| EP | 0 393 532 B1 | 10/1990 |
| EP | 0473502 | 3/1992 |

(List continued on next page.)

OTHER PUBLICATIONS

Partial Purification and Characterization of a Novel Soybean Protease Which is Inhibited by Kunitz and Bowman–Birk Trypsin Inhibitors: *J. Biochem. 119*, 711–178 (1996).

(List continued on next page.)

*Primary Examiner*—Frederick Krass
*Assistant Examiner*—Donna Jagoe

(57) ABSTRACT

This invention relates to methods and compositions for bringing about changes in skin pigmentation. More particularly, this invention relates to compounds which affect melanogenesis and can be used as depigmenting agents or as agents for darkening skin utilizing the PAR-2 pathway.

10 Claims, 6 Drawing Sheets

(4 of 6 Drawing Sheet(s) Filed in Color)

U.S. PATENT DOCUMENTS

| | | | |
|---|---|---|---|
| 5,231,090 A | 7/1993 | Hsia | 514/78 |
| 5,248,495 A | 9/1993 | Patterson | 424/73 |
| 5,254,331 A | 10/1993 | Mausner | 424/59 |
| 5,260,065 A | 11/1993 | Mathur | 424/450 |
| 5,270,042 A | 12/1993 | Whitham | 424/401 |
| 5,276,058 A | 1/1994 | Satoh | 514/646 |
| 5,306,444 A | 4/1994 | Kitamura | 510/490 |
| 5,310,734 A | 5/1994 | Losch | 514/78 |
| 5,322,839 A | 6/1994 | Voegeli | 514/21 |
| 5,352,443 A | 10/1994 | Kubo | 424/72 |
| 5,362,494 A | 11/1994 | Zysman | 424/401 |
| 5,364,886 A | 11/1994 | Loliger | 514/772 |
| 5,393,519 A | 2/1995 | Dowell | 424/70 |
| 5,397,497 A | 3/1995 | Jakobson | 252/170 |
| 5,407,675 A | 4/1995 | Etemad-Moghadam | 424/401 |
| 5,411,742 A | 5/1995 | Sebag | 424/450 |
| 5,427,814 A | 6/1995 | Loliger | 426/610 |
| 5,428,026 A | 6/1995 | Colarow | 514/78 |
| 5,438,044 A | 8/1995 | Losch | 514/78 |
| 5,439,672 A | 8/1995 | Zabotto | 424/59 |
| 5,443,839 A | 8/1995 | Meybeck | 424/450 |
| 5,443,840 A | 8/1995 | Morancais | 424/450 |
| 5,466,452 A | 11/1995 | Whittle | 424/750 |
| 5,498,420 A | 3/1996 | Mentrup Edgar | 424/450 |
| 5,523,308 A | 6/1996 | Costanzo | 514/317 |
| 5,539,129 A | 7/1996 | Zysman | 549/430 |
| 5,545,399 A | 8/1996 | Lee et al. | 424/59 |
| 5,547,661 A | 8/1996 | Sun | 424/66 |
| 5,567,420 A | 10/1996 | McEleney | 424/60 |
| 5,569,663 A | 10/1996 | Ribier | 514/315 |
| 5,571,503 A | 11/1996 | Mausner | 424/59 |
| 5,578,297 A | 11/1996 | Mellul | 424/70 |
| 5,589,181 A | 12/1996 | Bencsits | 424/405 |
| 5,595,984 A | 1/1997 | Blank | 514/159 |
| 5,597,814 A | 1/1997 | Blank | 514/159 |
| 5,601,833 A | 2/1997 | Roboer | 424/401 |
| 5,603,949 A | 2/1997 | Meybeck | 424/450 |
| 5,605,894 A | 2/1997 | Blank | 514/159 |
| 5,607,666 A | 3/1997 | Masson | 424/69 |
| 5,607,692 A | 3/1997 | Ribier | 424/450 |
| 5,614,180 A | 3/1997 | Chung | 424/70 |
| 5,614,215 A | 3/1997 | Ribier | 424/450 |
| 5,616,572 A | 4/1997 | Blank | 514/159 |
| 5,618,522 A | 4/1997 | Kaleta | 424/60 |
| 5,620,692 A | 4/1997 | Potter | 424/401 |
| 5,622,690 A | 4/1997 | Potter | 424/59 |
| 5,626,868 A | 5/1997 | Morancais | 424/450 |
| 5,629,015 A | 5/1997 | Ribier | 424/450 |
| 5,629,301 A | 5/1997 | Blank | 514/159 |
| 5,631,318 A | 5/1997 | Ito | 524/590 |
| 5,635,165 A | 6/1997 | Panitch | 424/65 |
| 5,637,316 A | 6/1997 | Ribier | 424/450 |
| 5,639,785 A | 6/1997 | Kung | 514/456 |
| 5,641,509 A | 6/1997 | Gross | 424/450 |
| 5,643,583 A | 7/1997 | Voultoury | 424/401 |
| 5,643,587 A | 7/1997 | Scancarella | 424/401 |
| 5,643,601 A | 7/1997 | Gross | 424/401 |
| 5,650,166 A | 7/1997 | Ribier | 424/450 |
| 5,652,230 A | 7/1997 | Blank | 514/159 |
| 5,653,988 A | 8/1997 | Gerber | 424/401 |
| 5,660,853 A | 8/1997 | Hansenne-Richoux | 424/450 |
| 5,665,367 A | 9/1997 | Burger | 424/401 |
| 5,674,511 A | 10/1997 | Kacher | 424/401 |
| 5,676,935 A | 10/1997 | Mellul | 424/61 |
| 5,676,956 A | 10/1997 | Duffy | 424/401 |
| 5,679,374 A | 10/1997 | Fanchon | 424/450 |
| 5,681,852 A | 10/1997 | Bissett | 514/566 |
| 5,683,683 A | 11/1997 | Scafidi | 424/70 |
| 5,686,102 A | 11/1997 | Gross | 424/450 |
| 5,691,327 A | 11/1997 | Blank | 514/159 |
| 5,723,148 A | 3/1998 | Love | 424/450 |
| 5,741,496 A | 4/1998 | Khaiat | 424/401 |
| 5,753,612 A | 5/1998 | Mitrani | 514/2 |
| 5,755,814 A | 5/1998 | Berg | 623/66.1 |
| 5,762,916 A | 6/1998 | Ansmann | 424/70 |
| 5,766,628 A | 6/1998 | Nurnberg | 424/450 |
| 5,776,917 A | 7/1998 | Blank | 514/159 |
| 5,780,456 A | 7/1998 | Blank | 514/159 |
| 5,780,458 A | 7/1998 | Blank | 514/159 |
| 5,780,459 A | 7/1998 | Blank | 514/159 |
| 5,786,345 A | 7/1998 | Blank | 514/159 |
| 5,786,346 A | 7/1998 | Blank | 514/159 |
| 5,789,396 A | 8/1998 | Blank | 514/159 |
| 5,795,879 A | 8/1998 | Blank | 514/159 |
| 5,801,163 A | 9/1998 | Blank | 514/159 |
| 5,804,216 A | 9/1998 | Terren | 424/450 |
| 5,807,545 A | 9/1998 | Coffindaffer | 424/70 |
| 5,824,702 A | 10/1998 | Wei | 514/456 |
| 5,833,965 A | 11/1998 | Sun | 424/66 |
| 5,834,013 A | 11/1998 | Ribier | 424/450 |
| 5,840,717 A | 11/1998 | Blank | 514/159 |
| 5,843,926 A | 12/1998 | Blank | 514/159 |
| 5,863,546 A | 1/1999 | Swinehart | 424/401 |
| 5,869,470 A | 2/1999 | Blank | 514/159 |
| 5,871,743 A | 2/1999 | Chajuss | 424/195 |
| 5,880,314 A | 3/1999 | Shinomiya | 568/729 |
| 5,885,593 A | 3/1999 | Epstein | 424/401 |
| 5,885,596 A | 3/1999 | Parab | 424/401 |
| 5,885,600 A | 3/1999 | Blum | 424/405 |
| 5,885,617 A | 3/1999 | Jordan | 424/474 |
| 5,885,948 A | 3/1999 | Glenn | 510/130 |
| 5,908,618 A | 6/1999 | Lorant | 424/70 |
| 5,916,577 A | 6/1999 | Golz | 424/401 |
| 5,928,654 A | 7/1999 | Duranton | 424/401 |
| 5,928,658 A | 7/1999 | Kishida | 424/401 |
| 5,928,889 A | 7/1999 | Bakich | 435/29 |
| 5,942,479 A | 8/1999 | Frankenback | 510/159 |
| 5,945,095 A | 8/1999 | Mougin | 424/78 |
| 5,945,109 A | 8/1999 | Schmidt | 424/401 |
| 5,952,373 A | 9/1999 | Lanzendorfer | 514/456 |
| 5,958,387 A | 9/1999 | Bara | 424/69 |
| 5,961,980 A * | 10/1999 | Kennedy et al. | 424/195.1 |
| 5,962,015 A | 10/1999 | Delrieu | 424/450 |
| 5,962,441 A | 10/1999 | Blank | 514/159 |
| 5,965,153 A | 10/1999 | Allen | 424/442 |
| 5,981,450 A | 11/1999 | Fabry | 510/127 |
| 5,985,338 A | 11/1999 | Suh | 426/69 |
| 5,985,809 A | 11/1999 | Frankenback | 510/159 |
| 5,990,291 A | 11/1999 | Waggle | 536/8 |
| 6,004,915 A | 12/1999 | Elliott | 510/135 |
| 6,013,250 A | 1/2000 | Cannell | 424/70 |
| 6,013,255 A | 1/2000 | Edens | 424/94 |
| 6,017,893 A | 1/2000 | Segelman | 514/27 |
| 6,019,962 A | 2/2000 | Rabe | 424/64 |
| 6,030,931 A | 2/2000 | Vinski | 510/130 |
| 6,033,680 A | 3/2000 | Dixon | 424/401 |
| 6,045,779 A | 4/2000 | Mueller | 424/47 |
| 6,048,520 A | 4/2000 | Hoshowski | 424/70 |
| 6,051,602 A | 4/2000 | Bissett | 514/456 |
| 6,054,137 A | 4/2000 | Breton | 424/400 |
| 6,060,070 A | 5/2000 | Gorbach | 424/401 |
| 6,063,398 A | 5/2000 | Gueret | 424/443 |
| 6,093,411 A | 7/2000 | Bissett | 424/401 |
| 6,180,662 B1 | 1/2001 | Lanzendorfer | 514/456 |
| 6,183,761 B1 | 2/2001 | Bissett | 424/401 |

FOREIGN PATENT DOCUMENTS

| | | |
|---|---|---|
| EP | 0 574 352 A1 | 12/1993 |
| EP | 0 643 083 B1 | 3/1995 |
| EP | 0 655 470 B1 | 5/1995 |
| EP | 273202 | 6/1995 |

| | | | |
|---|---|---|---|
| EP | 0707851 | 4/1996 | |
| EP | 0 713 106 A1 | 5/1996 | |
| EP | 0 758 687 A1 | 2/1997 | |
| EP | 0774249 | 5/1997 | |
| EP | 0811595 | 12/1997 | |
| EP | 0 814 116 A1 | 12/1997 | |
| EP | 0 963 761 A1 | 12/1999 | |
| EP | 1 074 240 A2 | 2/2001 | |
| EP | 1077 063 A2 | 2/2001 | |
| JP | 58-225003 | 6/1982 | |
| JP | 58-225003 | 12/1983 | A61K/7/00 |
| JP | 85-122134 | 6/1985 | C61K/7/00 |
| JP | 63-68512 | 9/1986 | |
| JP | 6-2036304 A | 2/1987 | |
| JP | 63-68512 | 3/1988 | A61K/7/00 |
| JP | 63-96120 | 4/1988 | |
| JP | 63-227515 | 9/1988 | |
| JP | 63-316711 | 12/1988 | |
| JP | 3-127713 | 10/1989 | |
| JP | 3-127713 | 5/1991 | A61K/7/00 |
| JP | 5-320061 | 5/1991 | |
| JP | 5-320024 | 5/1992 | |
| JP | 4-169514 | 6/1992 | A61K/7/00 |
| JP | 5-213729 | 8/1993 | |
| JP | 5-246932 | 9/1993 | |
| JP | 5-320024 | 12/1993 | A61K/7/00 |
| JP | 8-20597 | 7/1994 | |
| JP | 409025214 A * | 1/1997 | |
| KR | 92-8851 | 10/1992 | |
| RU | 2066992 | 9/1996 | |
| WO | WO 91/04283 | 4/1991 | |
| WO | WO 91/07166 | 5/1991 | |
| WO | WO 92/09639 | 6/1992 | |
| WO | WO 92/09650 | 6/1992 | |
| WO | WO 94/06485 | 3/1994 | |
| WO | WO 95/04609 | 2/1995 | |
| WO | WO 96/19483 | 6/1996 | |
| WO | WO 96/19491 | 6/1996 | |
| WO | WO 96/24371 | 8/1996 | |
| WO | WO 96/24392 | 8/1996 | |
| WO | WO 96/30035 | 10/1996 | |
| WO | WO 96/30396 | 10/1996 | |
| WO | WO 96/31194 | 10/1996 | |
| WO | WO 96/37497 | 11/1996 | |
| WO | WO 97/11033 | 3/1997 | |
| WO | WO 97/18904 | 5/1997 | |
| WO | WO 93/39733 A1 | 10/1997 | |
| WO | WO 97/35998 | 10/1997 | |
| WO | WO 98/02134 | 1/1998 | |
| WO | WO 98/05333 | 2/1998 | |
| WO | WO 98/08503 | 3/1998 | A61K/31/35 |
| WO | WO 98/09987 | 3/1998 | |
| WO | WO 98/33089 | 7/1998 | |
| WO | WO 98/49153 | 11/1998 | C07D/311/36 |
| WO | WO 99/04752 A2 | 2/1999 | |
| WO | WO 99/15917 | 4/1999 | |
| WO | WO 99/24003 | 5/1999 | A61K/7/06 |
| WO | WO 99/30729 A1 | 6/1999 | |
| WO | WO 99/36050 | 7/1999 | A61K/7/48 |
| WO | WO 99/57178 | 11/1999 | |
| WO | WO 00/15188 | 3/2000 | |
| WO | WO 00/51554 A3 | 9/2000 | |
| WO | WO 00/62740 A2 | 10/2000 | |
| WO | WO 00/62741 A2 | 10/2000 | |
| WO | WO 00/62743 A3 | 10/2000 | |
| WO | WO 00/62744 A3 | 10/2000 | |
| WO | WO 00/62745 A3 | 10/2000 | |
| WO | WO 00/69404 A1 | 11/2000 | |
| WO | WO 00/69406 A1 | 11/2000 | |
| WO | WO 00/69407 A1 | 11/2000 | |
| WO | WO 00/69408 A1 | 11/2000 | |

OTHER PUBLICATIONS

The Complete Amino Acid Sequence of Rice Bran Trypsin Inhibitor: *J. Biochem 102,* 2970–306 (1987).

Wheat Germ Trypsin Inhiboors. Isolation and Structural Characterization of Single–Headed and Double–Headed Inhibitors of the Bowman–Birk Type: *J. Biochem 100,* 975–983 (1986).

Aqueous Ethanol Extraction of Soybean Trypsin Inhibitors and Characterization of a Calcium–Sensitive: Keshun Liu, *Journal of Food Biochemistry 15 (1991) 159–168.*

Amino Acid Sequence and Secondary Structural Analysis of the Corn Inhibitor of Trypsin and Activated Hageman Factor, Walter C. Mahoney:: *Journal of Biological Chemistry,* vol. 259, No. 13 Jul. 10, 1984, 8412–8416.

Trypsin Inhibitor Polymorphism: Multigene Family Expression and Posttranslational Modification, Laurence Quillien: *Journal of Protein Chemistry,* vol. 16, No. 3 (1997) 195–203.

Inhibition of Serine Proteases of the Blood Coagulation System by Squash Family Protease Inhibitors, Kaeko Hayaski: *J. Biochem. 116,* 1013–1018 (1994).

Primary Structure of a Kunitz–Type Trypsin Inhibitor From *Enterolobium Contortisiliquum* Seeds, I.F.C. Batista: *Phytochemistry vol. 41,* No. 4, (1996) 1017–1022.

Amino Acid Sequences of Double–headed Proteinase Inhibitors from the Seeds of *Canavalia lineata,* Shigeyuki Terada: *Biosci. Biotech. Biochem. vol. 58,* (2) 376–379 (1994).

The biochemistry and nutrition group: 30 years of research in a developing country, Abraham Levy Benshimol: *Archivos LatinoAmericanos De Nutrician,* vol. 44, No. 4–S, pp 6–S–9–S (1994).

High–Performance Liquid Chromatographic Analysis of Phytoestrogens in Soy Protein Preparations with Ultraviolet Electrochemical and Thermospray Mass spectrometric Detection, K.D. R. Setchell: *Journal of Chromotography 386 (1987) 315–323.*

Interactions of Proteases with Legume Seed Inhibitors. Molecular features, Dinah S. deSeidl: *Archivos LatinoAmericanos de Nutricion,* vol. 44 No. 4–S (1994) 21–S–25–S.

Soy Intake and Cancer Risk: A Review of the InVitro and InVivo Data, Mark J. Messina: *Nutrician and Cancer vol. 21,* No. 2, (1994) 113–131.

The Use of Thermospray Liquid Chromatography/Tandem Mass spectrometry for the Class Identification and Structural Verification of Phytoestrogens in Soy Protein Preparations, Robert J. Barbuch: *Biomedical and Environmental Mass Spectrometry,* vol. 18, (1989) 973–977.

Defining Food Components as New Nutrients, Suzanne Hendrick: *American Institute of Nutrition (1994) 1789S–1792S.*

Relevance of Multiple Soybean Trypsin Inhibitor Forms to Nutritional Quality, Anna L. Tan–Wilson, Department of Biological Sciences, State University of New York at Binghamton, 391–411.

Nutrition Communique Soy: Just a Hill of Beans? Clare M. Hasler: *Journal of women's Health,* vol. 7, No. 5 (1998) 519–523.

Protein Proteinase inhibitors in legume seeds—Overview, Yehudith Birk: *Archivos Latinoamericanos de Nutricion,* vol. 44, No. 4–S (1994) 26–S–30–S.

The Effect of a Drug–delivery System Consisting of Soybean Phosphatidyl Choline and Medium–chain Monoacylglycerol on the Intestinal Permeability of Hexarelin in the Rat, Urban Fagerholm: *J. Pharm. Pharmacol (1998) 50:* 467–473.

A Serine Protease From Suspension–Cultured soybean Cells, Ze–Jian Guo: *Phytochemistry*, vol. 47, No. 4 (1998) 547–553.

Trypsin Inhibitor Activity in Commercial Soybean Products in Japan, Yuko Miyagi: *J. Nutr. Sci. Vitaminol (1997) vol. 43: 575–580.*

Soy–derived protease inhibitors treat cancer and inflammation, Louis J. Scotti: Windhover Information Inc. (1998).

Crystal Structure of the Complex of Porcine Pancreatic Trypsin with Kunitz–Type Soybean Trypsin Inhibitor, Hyun K. Song: www.bmsc.wahing...ts/abstracts/S0081.html.

Two Groups of Protease Inhibitors Functionally Active in Buckwheat Seeds, Yakov Dunaevsky: soba.shinshu–uac.jp/contents/105.html.

Isolation and Properties of Anionic Protease Inhibitors from Buckwheat Seeds, Y.E. Dunaevsky: *Biochemistry and Molecular Biology International,* vol. 40, No. 1, (1996) 199–208.

Effect of Heat Treatments on Trypsin/Chyomotrypsin Inhibitor Activity of Red Gram (*Cajanus Cajan* L.), V.H. Mulimani: *Plant Foods for Human Nutrition,* vol. 46, No. 2, ((1994) 103–107.

Effects of heat treatment and germination on trypsin and chymotrypsin inhibitory activities in sorghum (*sorghum bicolor* (L.) Moench) seeds, V.H. Mulimani: *Plant Foods for Human Nutrition,* vol. 44, No. 3 (1993) 221–226.

Avon's Anew Positivity Trio Targets Menopausal Women : *The Rose Sheet,* Feb. 28, 2000, p 8.

Soybean Technology Improves Skin: *Cosmetics & Toiletries,* vol. 115, No. 3, (2000) 22.

Evaluation of the Effects of Hair Re–growth substances on Elongation of Anagen Period and Blockade of Anagen–Catagen Transformation, Kazuto Hamada: *J. Soc. Cosmet. Chem. Japan,* vol. 31, No. 4 (1997) 1–3.

Current problem of research on hair growth mechanisms and hair growth promoters, Hideki Ogawa:*Fragrance Journal (1985( vol. 5, 1–5.*

Brochure on Lipoxydase Code 411784, Apr. 1999.

Product Brochure on Elhibin.

Brochure for Anti–regrowth effect of hair: Dec. 22, 1998.

Phtoestrogen Content of Processed Soybean Products, P.A. Murphy: *Food Technology,* vol. 1, 60–64 (1982).

Soy Therapy, www.wiseessentials.com/ (Apr. 13, 2000).

The Bowman–Birk Inhibitor, Y. Birk: *Am. J. Peptide Protein:* 1985, 113–131.

Product for Damaged hair by Bristol–Myers Squibb, Y. Mashiko.

U.S. patent application Ser. No. 09/110,409, Johnson & Johnson.

U.S. patent application Ser. No. 09/361,426, Johnson & Johnson.

Amino Acid Sequence and Secondary Structural Analysis of the Corn Inhibitor of Trypsin and Activated Hageman Factor, Walter C. Mahoney:: Journal of Biological Chemistry, vol. 259 No. 13 Jul. 10, 1984, 8412–8416.

Amino Acid Sequences of Double–headed Proteinase Inhibitors from the Seeds of Canavalia lineata, Shigeyuki Terada: Biosci. Biotech. Biochem. vol. 58, (2) 376–379 (1994).

A Serine Protease From Suspension–Cultured soybean Cells, Ze–Jian Guo: Phytochemistry, vol. 47, No. 4 (1998) 547–553.

Aqueous Ethanol Extraction of Soybean Trypsin Inhibitors and Characterization of a Calcium–Sensitive: Keshun Liu, Journal of Food Biochemistry 15 (1991) 159–168.

Cardiovascular and Renal Small molecule direct thrombin inhibitors, Wiley and Fisher, Ashley Publications, Ltd. 1997, pp. 1265–1282.

Defining Food Components as New Nutrients, Suzanne Hendrick: American Institute of Nutrition (1994) 1789S–1792S.

Effect of Heat Treatments on Trypsin/Chyomotrypsin Inhibitor Activity of Red Gram (Cajanus Cajan L.), V.H. Mulimani: Plant Foods for Human Nutrition, vol. 46, No. 2, (1994) 103–107.

Effects of heat treatment and germination on trypsin and chymotrypsin inhibitory activities in sorghum (Sorghum bicolor (L.) Moench) seeds, V.H. Mulimani: Plant Foods for Human Nutrition, vol. 44, No. 3 (1993) 221–226.

Evaluation of the Effects of Hair Re–growth Agents on Lengthening the Anagen Phase Period and Blockade of Anagen phase–Catagen phase Transformation, Kazuto, J. Soc. Cosmet. Chem Japan, vol. 31 No. 4(1997):413–419.

High–Performance Liquid Chromatographic Analysis of Phytoestrogens in Soy Protein Preparations with Ultraviolet Electrochemical and Thermospray Mass spectrometric Detection, K.D. R. Setchell: Journal of Chromotography 386 (1987) 315–323.

Isolation and Properties of Anionic Protease Inhibitors from Buckwheat Seeds, Y.E. Dunaevsky: Biochemistry and Molecular Biology International, vol. 40, No. 1, (1996) 199–208.

Inhibition of Serine Proteases of the Blood Coagulation System by Squash Family Protease Inhibitors, Kaeko Hayaski: J. Biochem. 116, 1013–1018 (1994).

Interaction of Proteases with Legume Seed Inhibitors. Molecular features, Dinah S. deSeidl: Archivos Latinoamericanos de Nutricion, vol. 44 No. 4–S (1994) 21–S–25–S.

Partial Purification and Characterization of a Novel Soybean Protease Which is Inhibited by Kunitz and Bowman–Birk Trypsin Inhibitors, Shimpei Morita, vol. 119, No. 4, 1996 pp. 711–718.

Phytoestrogen Content of Processed Soybean Products, P.A. Murphy: Food Technology, vol. 1, 60–64 (1982).

Primary Structure of a Kunitz–Type Trypsin Inhibitor From Enterolobium Contortisiliquum Seeds, I.F.C. Batista: Phytochemistry vol. 41, No. 4, (1996) 1017–1022.

Soy Intake and Cancer Risk: A Review of the InVitro and InVivo Data, Mark J. Messina: Nutrician and Cancer vol. 21, No. 2, (1994) 113–131.

The Complete Amino Acid Sequence of Rice Bran Trypsin Inhibitor: J. Biochem 102, 2970–306(1987).

The biochemistry and nutrition group:30 years of research in a developing country, Abraham Levy Benshimol: Archivos Latino–Americanos De Nutrician, vol. 44, No. 4–S, pp 5–S–9–S (1994).

The Effect of a Drug–delivery System Consisting of Soybean Phosphatidyl Chloline and Medium–chain Monoacylglycerol on the Intestinal Permeability of Hexarelin in the Rat, Urban Fagerholm: J. Pharm. Pharmacol (1998) 50: 467–473.

The Use of Thermospray Liquid Chromatography/Tandem Mass spectrometry for the Class Identification and Structural Verification of Phytoestrogens in Soy Protein Preparations, Robert J. Barbuch: Biomedical and Environmental Mass Spectrometry, vol. 18, (1989) 973–977.

Trypsin Inhibitor Polymorphism: Multigene Family Expression and Posttranslational Modification, Laurence Quillen: Journal of Protein Chemistry, vol. 16, No. 3 (1997) 195–203.

Trypsin Inhibitor Activity in Commercial Soybean Products in Japan, Yuko Miyagi: J. Nutr. Sci. Vitaminol (1997) vol. 43:575–580.

Two Groups of Protease Inhibitors Functionally Active in Buckwheat Seed, Yakov Dunaevsky: soba.shinshu–uac.jp/contents/105.html, publicly available prior to Feb. 28, 2001.

Wheat Germ Trypsin Inhiboors. Isolation and Structural Characterization of Single–Headed and Double–Headed Inhibitors of the Bowman–Birk Type: J. Biochem 100, 975–983 (1986).

The Joy of Soy: www.wheat–grass.com/851_oral_liquid.shtml, Wheatgrass Express, Inc. 1996.

Concerns Regarding Soybeans: www. rheumatic.org/soy.htm, publicly available prior to Feb. 28, 2001.

Soy Therapy, www.wiseesentials. com/soytherapy.html (Apr. 13, 2001).

Elhibin –Brochure, Centerchem, Inc., publicly available prior to Feb. 28, 2001.

Soybean Technology Improves Skin, Allured's Cosmetics & Toiletries Magazine vol. 115, No., 3. Mar. 2000, p. 22.

Abstract for Product for Damaged hair by Bristol–Myers–Squibb, publicly available prior to Feb. 28, 2001.

"CaspACE Assay System, Colorimetric," Product Improvements, Neural Notes vol. V, Issue 1 1999, p. 13.

Piotr Chomczynski & Nicoletta Sacchi, "Single–Step Method of RNA Isolation by Acid Quanidinium Thiocyanate–Phenol–Chloroform Extraction," Analytical Biochemistry 162, 156–159 (1987), Copyright 1987 by Academic Press, Inc.

Ann R. Kennedy, Department of Radiation Oncology, University of PA School of Medicine, Philadelphia, PA 19104, USA, "Chemopreventive Agents: Protease Inhibitors," Pharmacol. Ther. 78(3): 167–209, 1998, Copyright 1998 Elsevier Science Inc.

James M. Clark, William M. Abraham, Cindy E. Fishman, Rosanna Forteza, Ashfaq Ahmed, Alejandro Cortes, Robert L. Warne, William R. Moore, and Richard D. Tanaka, Dept. of Molecular Pharmacology, Inflammation Program, Arris Pharmaceutical Corp. Souch San Francisco, CA, and Department of Research, Division of Pulmonary Diseases, University of Miami at Mount Sinai Medical Center, Miami Beach, Florida Tryptase Inhibitors Block Allergen–induced Airway and Inflammatory Responses in Allergic Sheep, Am J. Respir Crit Care Med vol. 152, pp 2076–2083, 1995.

Jussara F. Molinari, Mario Scuri, William R. Moore, James Clark, Richard Tanaka, and William M. Abraham, Division of Pulmonary Disease, University of Miami at Mount Sinai Medical Center, Miami Beach, Florida and the Arris Pharmaceutical Corporation, South San Francisco, CA, "Inhaled Tryptase Causes Bronchoconstriction in Sheep Via Histamine Release", am J Respir Crit Care Med vol. 154 pp. 649–653, 1996.

Differential Regulation of Human Keratinocyte Growth and Differentiation by a Novel Family of Protease–activated Receptors, Claudia Derian; Cell Growth & Differentiation vol. 8, 743–749, Jul. 1997.

Influence of Nonionic Liposomal Composition on Topical Delivery of Peptide Drugs into Pilosebaceous Units: An in Vivo Study Using the Hamster Ear Model; Pharmaceutical Research, vol. 12, No. 8, 1995 pp. 1184–1188.

Potent Thrombin Inhibitors That Probe the S1 Subsite; Tripeptide Transition State Analogues Based on a Heterocycle–Activated Carbonyl Group, Journal Medical Chem., 1996, 39, 3039–3043.

Cardiovascular and Renal Small molecule direct thrombin inhibitors, Wiley and Fisher, Ashley Publications, Ltd., 1997, pp. 1265–1282.

Avon's Anew Positivity Trio Targets Menopausal Women, The Rose Sheet, Feb. 28, 2000, p.8.

Abstract of WO 99/36050 Novogen Research Pty LTD Jul. 1999.

"Superscript II Reverse Transcriptase" protocol pub. by Gibco–BRL (now Life Tech Inc) Apr. 1992*.

"Evidence for the Presence of a Protease–Activated Receptor Distinct from the Thrombin Receptor in Human Keratinocytes" R.J. Santulli et al. Proceeding of the National Academy of Sciences of USA, vol. 92, Sep. 1995, pp. 9151–9155.

"Interactions of Mast Cell Tryptase with Thrombin Receptors and PAR–2" M. Molino et al. Journal of Biological Chemistry, vol. 272, No. 7, Feb. 14, 1997 pp. 4043–4049.

Billings et al., Pro. Natl. Acad. Sci. 89:3120–3124 (1992)*.

"The Bowman–Birk Inhibitor", Int. J. Pept. Protein Res. 25:113–131 (1985).

Kennedy, Am. J. Clin. Neutr. 68:1406S–1412S (1998)*.

Liu, K., Chemistry and Nutritional value of soybean components. In: Soybeans, chemistry, technology and utilization pp. 32–35 (Aspen publishers, Inc., Gaithersburg, MD, 1999*.

Song et al., J. Mol. Biol. 275:347–63 (1998)*.

"Liposomes—A Selective Drug Delivery System for the Topical Route of Administration; Gel Dosage Form", Journal of Pharmaceutics and Pharmacology, vol. 34 (1982), pp.473–474*.

(EnzChek™ Protease Assay Kits Product Information, Revised Mar. 15, 1999; Molecular Probes, Eugene OR)*.

"Disinfection, sterilization, and preservation" 4th edition, Seymour S. Block, pp. 887–888 (1991, Lea & Febiger, Malvern, PA).*

"Official Compendia of Standards, USP 24 USP/NF 19", United States Pharmacopeial Convention, Inc. 2000 (Board of Trustees, United States Pharmacopeial Convention, Inc.)*.

"Official Methods of Analysis of AOAC International," edited Patricia Cunniff, Sixteenth Edition, $5^{th}$ Revision, 1999 (AOAC International)*.

A. Meister, Cancer Res. 54: 1969s–1975s (1994).

Current Protocols in Cell Biology, Edited by Juan S. Bonifacino et al. Chapter 6: Electrophoresis and Immunoblotting. Copyright 1999 by John Wiley & Sons, Inc.*.

D.P.T. Steenvoorden, et al., Photochem Photobiol. 67:651–656 (1998)*.

Handbook of Non–Invasive Methods and the Skin, eds. J. Serup & G. Jemec, Chapter 14.3 (1995).*

Jimenez, M., K., Maloy, WL, and Hearing, V. Specific identification of an authentic tyrosinase clone. J. Biol. Chem. (1989) 264:3397–3403*.

Jimenez, M., Kameyama, K., Maloy, WL, Tomita Y., and Hearing, V. Mammalian tyrosinase: biosynthesis, processing and modulation by melanocyte stimulating hormone. Proc. Natl. Acad. Sci. USA (1988), 85:3830–34*.

K. Hanada, et al., J. Invest. Dermatol. 108:727–730 (1997)*.
L. T. van den Broeke and G. M. J. Beijersbergen van Henegouwen, J. Photochem. Photobiol. B Biol. 27:61–65 (1995)*.
M. J. Connor and L.A. Wheeler, Photochem. Photobiol. 46:239–246 (1987)*.
McCutcheon's Detergents and Emulsifiers, North American Edition, pp. 317–324 (1986)*.
Mezei & Gulasekharam, "Liposomes—A Selective Drug Delivery System for the Topical Route of Administration; Gel Dosage Form", Journal of Pharmaceutics and Pharmacology, vol. 34 (1982), pp. 473–474*.
Mezei, M., "Liposomes as a Skin Drug Delivery System", Topics in Pharmaceutical Sciences (D.D. Breimer and P. Speiser, eds.,), Elsevier Science Publishers B. V., New York, N.Y., 1985, pp. 345–358*.
R. M. Tyrrell and M. Pidoux, Photochem. Photobiol. 47:405–412 (1988)*.
Sagarin, Cosmetics, Science and Technology, 2nd Edition, vol. 1, pp. 32–43 (1972)*.
Sagarin, Cosmetics, Science and Technology, 2nd Edition, vol. 1, pp. 72–73 (1972)*.
Stenn, et al., "Glucocorticoid Effect on Hair Growth Initiation: A Reconsideration," 6 Skin Pharmacol., 125–134 (1993)*.
Steenvoorden et al., "The Use of Endogenous Antioxidants to Improve Photoprotection" Journal of Photochemistry and Photobiology B:Biology 41 (1997) 1–10.
Chemical Abstracts, vol. 123, No. 21, Nov. 20, 1995 Columbus, Ohio, US; abstract No. 281641, XP002094580 & R.J. Santulli et al.: "Evidence for the presence of PAR.." Proc. Natl. Acad. Sci USA, vol. 92, No. 20, 1995, pp. 9151–9155.
Derwent Abstract of JP 09 025214 A, Jan. 1997.
Derwent Abstract of JP 04 169514 A, Jun. 1992.
Derwent Abstract of JP 09 025212 A, Jan. 1997.
Derwent Abstract of JP 08 199891 A, Apr. 1996.
Derwent Abstract of JP 08 012560 A, Jan. 1996.
Leukocytosis, Monocytosis and Neutrophilla; Hallmarks of Severe Depression. Maes, M., et al. J. Psychiat. Res. 1992, pp. 125–134.
Daizepam Inhibits Phaagocytosis and Killing Exerted by Polymorphonuclear cells and Monocytes from Healthy Donors. Abstract. Immunopharmacology and Immunotoxicology (1989) pp. 701–714.
Do Microglial Cells Phagocyte the B/A4–Amyloid Senile Plaque Core of Alzheimer Diesease? Hachimi, K. et al., Academy of Science, Paris. 1994, pp. 445–451.
Macrophage Uptake of Cholesterol–Containing Particles Derived from LDL and Isolated from Atherosclerotic Lesions. Hoff, H. F., et al. European Heart Jouenal, 1990, pp. 105–115.
Cell–Marix Interactions in the Genesis of Arteriosclerosis and Alateroma (Effect of Aging). Robert, L., et al. Laboratorie de Biologie du Tissu Conjonctif 1992, pp. 331–341.
Astrocytes Regulate Microglial Phagocytosis of Senile Plaque Cores of Alzheimers's Disease. DeWitt, David A., Institute of Pathology, 1998 pp. 329–340.
Protease–Activated G Protein Coupled Receptors on Human Platelets and Endothelial Cells. Brass, Lawrence F., et al. University of Pennsylvania, 1997, pp. 234–241.
Protease Activated Receptors Start a Family. Couglin, shaun R., University of California, 1994, pp. 9200–9202.
Mid–Dermal Elastolysis; An Ultrastructural and Biochemical Study. Fimiani, M., et al., Siena University, 1995, pp. 152–157.

Neutrophil and Monocyte Phagocytosis in Depressed Patients. McAdams C., et al. Neuro–Psychopharmacol & Bio. Psychiat, 1998 pp. 971–984.
Identification of Potential Activators of Proteinase–Activated Receptor–2. Fox, Mark T., et al. Federation of European Biochemical Societies. 1997. pp. 267–269.
Altered Cell Signaling and Mononuclear Phagocyte Deactivation During Interacellular Infection. Reiner, Neil E. Immunology Today. 1994. pp. 374–381.
Differential Regulation of Human Keratinocyte Growth and Differentiation by a Novel Family of Protease–Activated Receptors. Darian, Claudia K. et al. Cell Growth & Differentiation. 1997, pp. 743–749.
Potent Thrombin Inhibitors that Probe the S Subsite; Tripeptide Transition State Analogues Based on a Heterocycle Actived Carbonyl Grup. Costanzo, Michael j., et al. J. Med. Chem. 1996, pp. 3039–3043.
Adhesion Molecule Expression in Normal Skin and Melanocytic Lesions. Tronnier, Michael, et al. Journal of Cutaneous Pathology, 1997, pp. 278–285.
Common Disorders of Pigmentation. Hacker, Steven M., Postgraduate Medicine. 1996, pp. 177–186.
The Role of Neutrophil Elastase in Chronic Inflammation. Doring, Grd. Department of Genreal Hygience and Environmental Hygiene, 1994, pp. 114–117.
Inflammatory and Immune Responses are impaired in Mice Deficient in Intercellular Adhesion Molecule I. Sligh, James E., et al. Proc. Natl. Acad., Sci. 1993, pp. 8529–8533.
Subcellular Distribution of Tyrosinase and Tyrosinase–Related Protein–L; Implications for Melanosomal Biogenesis. Orlow, Seth J., et al. The Socieity for Investigative Dermatology, Inc. 1993, pp. 55–64.
Photocarcinogenesis and Inhibition of Intercellular Adhesion Molecular I Expression in Cells of DNA–Repair–Defective Individuals. Ahrens, C., et al. The National Academy of Sciences 1997, pp. 6837–6841.
Influence of Nonionic Lipsomal Composition on Topical Deliveyr of Peptide Drugs into Pilosebaceouos units; an in Vivo Study Using the Hamster Ear Model. Niemiec, S., et al. Pharmaceutical Research, 1995, pp. 1184–1188.
Inflammation in Acne Vulgaris. Webster, Guy F., Jefferson Medical College. 1995, pp. 247–253.
Adhesion Molecules Expression in Normal Skin and Melanocytic Lesions. Tronnier, M., et al., Medical University of Lubeck, Germany. 1996 pp. 278–285.
Intecellular Adhesion Molecule–1. Van de Stope, A., et al. University Hospital Nijmegen, The Netherlands. 1996 pp. 13–33.
Fluorescence Assay to Monitor Phagocytosis by Blood–Clot Derived Polymorphonuclear Leucocytes Study of Patients with Diabetes and Phagocytosis of Different Staphyloccoccal Species. Muxclow. C. Elizabeth et al., Mount Sinai Hospital, 1991, pp. 15–24.
The Role of Preteolytic Enzymes in the Development of Pumonary Emphysema and Periodontal Disease. Travis J., et al. University of Georgia and Institute of Molecular Biology. 1994, pp. S143–S146.
Immunologic Aspects of Lung Diseases and Cystic Fibrosis. Greenberger, Paul A. Jama, 1997, pp. 1924–1930.
Abstract of JP 07304655 Nov. 1995.
Abstract of WO 98/33089 A, Jul. 1998.
Leaflet from Ichimaru Pharcos issued Mar. 7, 1997 "Plant Extract Containing Female Hormone–like Isoflavones".

* cited by examiner

The Soybean derived proteins BBI and STI reduce pigmentation in the Yucatan Swine

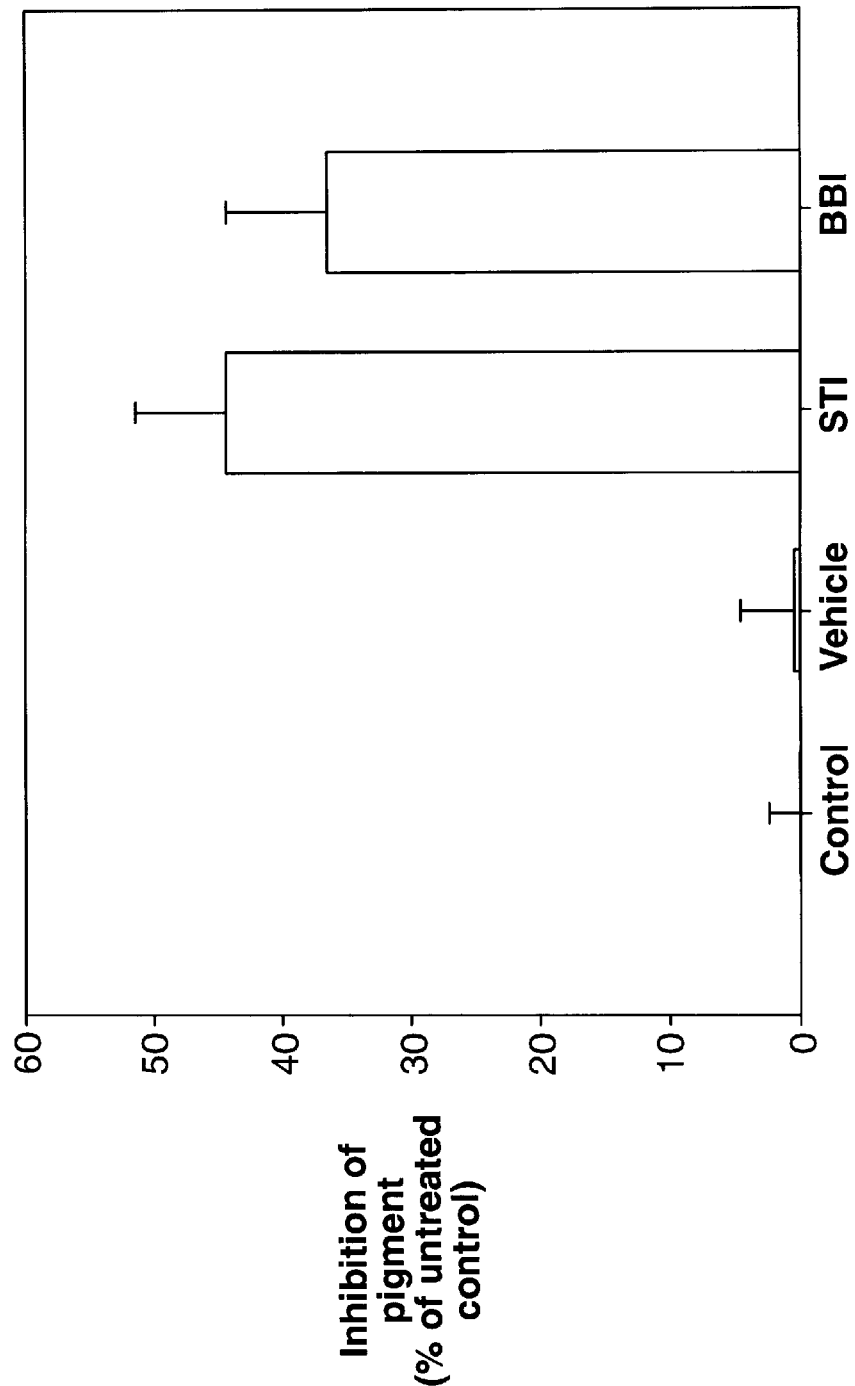

METHODS FOR TREATING SKIN PIGMENTATION

This is a continuation-in-part application of U.S. patent application Ser. No. 09/110,409, filed on Jul. 6, 1998, which is hereby incorporated herein by reference.

BACKGROUND

1. Field of the Invention

This invention is related to methods and compositions for bringing about skin pigmentation and/or for causing skin depigmentation. More particularly, this invention relates to compounds which affect melanogenesis and can be used as depigmenting agents or as agents for darkening skin.

2. Background of the Invention

Skin coloring has been of concern to human beings for many years. In particular, the ability to remove hyperpigmentation, such as found in age spots, freckles or aging skin generally, is of interest to individuals desiring a uniform complexion. In certain areas of the world, general body whitening is desirable. There are also hypopigmentation and hyperpigmentation disorders that are desirable to treat. Likewise, the ability to generate a tanned appearance without incurring photodamage due to solar radiation is important to many individuals. There have been many methods proposed to accomplish depigmentation, as well as to accomplish darkening of the skin. For example, kojic acid, hydqinone, retinoids and other chemical compounds have been used for depigmentation. Dihydroxyacetone and like chemical compounds have been utilized for their ability to "tan" the skin without exposure to the sun.

Many of these previous solutions have not been found acceptable. There is often a distinct line of demarcation between the areas of skin to which such previous compositions have been applied. Therefore, precise application of all these compounds is necessary in order to achieve the desired result. Many of these compounds have been found to be quite irritating to the skin and therefore undesirable for use.

The understanding of the chemical and enzymatic basis of melanogenesis is heavily documented. Melanocytes migrate from the embryonal neural crest into the skin to produce secretory granules, melanosomes, which produce melanin. Melanogenesis occurs within the melanosome, and the melanin is later distributed to keratinocytes via the melanocyte dendrites. The key enzyme in melanogenesis is tyrosinase, which initiates a cascade of reactions which convert tyrosine to the biopolymer melanin. Two tyrosinase-related proteins (TRP's) are known, TRP-1 and TRP-2. These proteins share with tyrosinase about 40% homology and have catalytic activities as well as regulatory roles in melanogenesis. TRP-1 is the most abundant glycoprotein in melanocytes.

In spite of the fact that the chemical and enzymatic basis of melanogenesis is well-documented, its regulation at the cellular level is only partially understood. Tyrosinase and the TRP's share structural and biological properties with the lysosomal-associated membrane protein (LAMP) gene family, therefore their targeting to the melanosomal membrane might induce their activation. A phosphorylation/dephosphorylation reaction at the cytoplasmic tails of these proteins could be involved in the regulation of melanogenesis. The beta isoform of the Protein Kinase C (PKC) family has been shown to regulate human melanogenesis through tyrosinase activation. Gene expression of tyrosinase, TRP-1 and TRP-2 is coordinated. All three enyzmes are expressed in human epidermis. In melanocytes co-cultured with keratinocytes, these transcripts are expressed at a ratio of 45:45:10, respectively. In melanocytes cultured alone, only TRP-1 transcripts are present, indicating that a kerainocyte-derived signal is involved in the coordinate expression of these genes. The regulation of keratinocyte-melanocyte interactions and the mechanism of melanosome transfer into keratinocytes are not yet understood.

The Protease-activated receptor-2 (PAR-2) is a seven transmembrane G-protein-coupled receptor, that is related to, but distinct from the thrombin receptors (TR also named PAR-1, and PAR-3) in its sequence. Both receptors are activated proteolytically by an arginine-serine cleavage at the extracellular domain. The newly created N-termini then activate these receptors as tethered ligands. Both receptors could be activated by trypsin, but only the TRs are activated by thrombin. Only PAR-2 is activated by mast cell tryptase. Both receptors could also be activated by the peptides that correspond to their new N-termini, independent of receptor cleavage. SLIGRL, the mouse PAR-2 activating peptide, is equipotent in the activation of the human receptor. While the function of the TR is well documented, the biology of the PAR-2 has not yet been fully identified. A role for PAR-2 activation in the inhibition of keratinocyte growth and differentiation has been recently described (Derian et al., "Differential Regulation of Human Keratinocyte Growth and Differentiation by a Novel Family of Protease-activate Receptors", *Cell Growth & Differentiation*, Vol. 8, pp. 743–749, July 1997).

SUMMARY OF THE INVENTION

In accordance with this invention, we have found a method for affecting changes in mammalian skin pigmentation comprising topically applying to the skin of a mammal a compound which affects the PAR-2 pathway. The compositions of this invention may contain one or more compounds that act as trypsin, as tryptase, as serine protease or as PAR-2 agonists, for increase in pigmentation. Alternatively, they may contain one or more compounds that act as serine protease inhibitors, trypsin inhibitors, thrombin inhibitors, tryptase inhibitors, as PAR-2 pathway inhibitors or as a PAR-2 antagonist for decrease in pigmentation, or "depigmentation".

As used herein, "mammal" means any member "of the higher vertebrate animals comprising the class "Mammalia", as defined in Webster's Medical Desk Dictionary 407 (1986), and includes but is not limited to humans. As used herein, "receptor" shall include both intracellullar and extra-cellular receptors and shall mean those molecules capable of receiving and transducing a signal. The term PAR-2 refers to the protease-activated receptor-2 or a related protease activated receptor. The Protease-activated receptor-2 (hereinafter, "PAR-2") is a serine-protease activated receptor that is expressed in numerous tissues, including keratinocytes and fibroblasts. The thrombin receptor (also named PAR-1, hereinafter, "TR") is a serine-protease activated receptor that is expressed in numerous tissues, including keratinocytes. The biological roles of PAR-2 and TR in skin are not entirely known. However, we have found that interactions between keratinocytes and melanocytes, via the PAR-2 pathway, affect melanogenesis. We have found that thrombin inhibitors, and/or tryptase inhibitors, and/or trypsin inhibitors and PAR-2 antagonists can be used as depigmenting agents without irritation of the skin. PAR-2 agonists and serine proteases such as trypsin and tryptase can be used as darkening agents. Furthermore, PAR-2 could be useful as a target for whitening and darkening agents.

We have further discovered that BBI, a Bowman-Birk type inhibitor, may also be used as an active depigmenting agent. Soybean-derived extracts and mixtures that were suggested in U.S. patent application Ser. No. 09/110,409 as depigmenting agents contain both STI and BBI. We have now found that BBI alone is effective to depigment skin. BBI may be used in all the formulations and compositions set forth in the parent application in the same range of concentration as STI.

BRIEF DESCRIPTION OF THE DRAWINGS

The patent contains at least one drawing executed in color. Copies of this patent with color drawing will be provided by the Patent and Trademark Office upon request and payment of the necessary fee.

FIG. 6 is a graph of computerized image analysis of pigment deposition in skin sections such as those demonstrated in FIG. 5. The graph quantifies the percent of inhibition of pigment deposition in the swine skin following BBI or STI treatment.

DETAILED DESCRIPTION OF THE PREFERRED EMBODIMENTS

Figure 1:
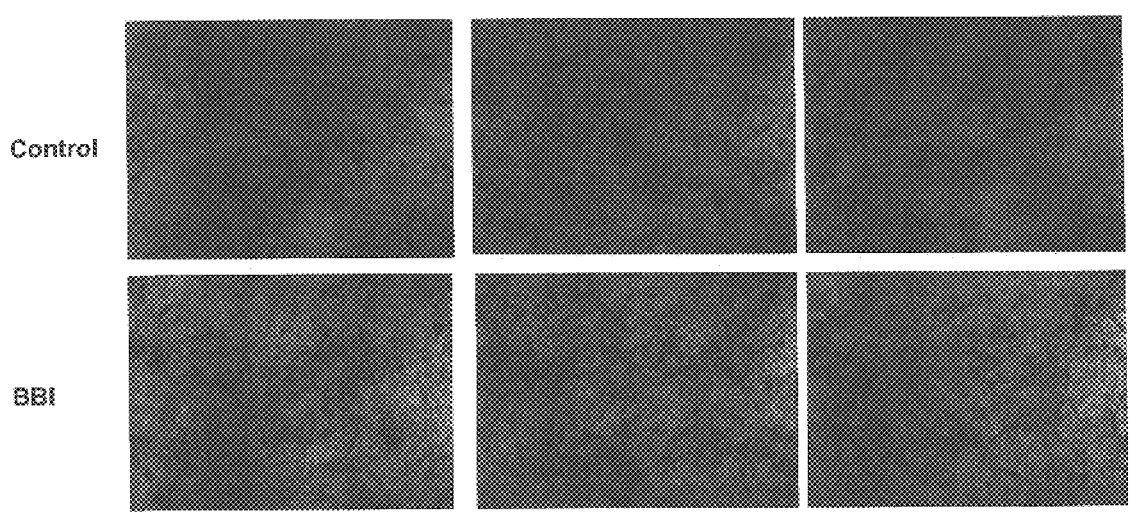
FIG. 1 shows epidermal equivalents containing melanocytes of an African-American donor. Treatment with BBI reduces pigment deposition in these equivalents, as demonstrated by top view of the equivalents, with no staining.

We have discovered that trypsin, tryptase and PAR-2 agonists can be used to increase pigmentation and that trypsin inhibitors, and/or tryptase inhibitors, and/or thrombin inhibitors and PAR-2 antagonists act to decrease pigmentation in mammalian skin. In our opinion, some of the compounds described in U.S. Pat. No. 5,523,308, which is hereby incorporated herein by reference, and behave as thrombin and/or trypsin and/or tryptase inhibitors, will be useful in methods of this invention. Some of these compounds are also described in Costanzo, et al., "Potent Thrombin Inhibitors That Probe the $S_1'$ Subsite: Tripeptide Transition State Analogues Based on a Heterocyde-Activated Carbonyl Group", *J. Med. Chem*, 1996, Vol. 39, pp. 303–3043 and have the following structural formula:

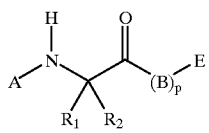

wherein:

A is selected from the group consisting of $C_{1-8}$alkyl, carboxy$C_{1-4}$alkyl, $C_{1-4}$alkoxycarbonyl$C_{1-4}$alkyl, phenyl$C_{1-4}$alkyl, substituted phenyl$C_{1-4}$alkyl (where the phenyl substituents are independently selected from one or more of, $C_{1-4}$alkyl, perfluoro$C_{1-4}$alkyl, $C_{1-4}$alkoxy, hydroxy, halo, amido, nitro amino, $C_{1-4}$alkylamino, $C_{1-4}$dialkylamino, carboxy or $C_{1-4}$alkoxycarbonyl), formyl, $C_{1-4}$alkoxycarbonyl, $C_{1-2}$alkylcarbonyl, phenyl$C_{1-4}$alkoxycarbonyl, $C_{3-7}$cycloalkylcarbonyl, phenylcarbonyl, substituted phenylcarbonyl (where the phenyl substituents are independently selected from one or more of, $C_{1-4}$alkyl, perfluoro$C_{1-4}$alkyl, $C_{,1-4}$alkoxy, hydroxy, halo, amido, nitro, amino, $C_{1-4}$alkylamino, $C_{1-4}$dialkylamino, carboxy or $C_{1-4}$alkoxycarbonyl), $C_{1-4}$alkylsulfonyl, $C_{1-4}$alkoxysulfonyl, perfluoro$C_{1-4}$alkyl-sulfonyl, phenylsulfonyl, substituted phenylsulfonyl (where the phenyl substituents are independently selected from one or more of, $C_{1-4}$alkl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), 10-camphorsulfonyl, phenyl$C_{1-4}$alkysulfonyl, substituted phenyl$C_{1-4}$alkysulfonyl, $C_{1-4}$alkylsulfinyl, perfluro$C_{1-4}$alkylsulfinyl, phenylsulfinyl, substituted phenylsulfinyl (where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), phenyl$C_{1-4}$alkylsulfinyl, substituted pehnyl$C_{1-4}$alkylsulfinyl, 1-naphthylsulfonyl, 2-naphthylsulfonyl or substituted naphthylsulfonyl (where the naphthyl substituents are independently selected from one or more of, $C_{1-4}$alkyl, perfluoro$C_{1-4}$alkyl, $C_{1-4}$alkoxy, hydroxy, halo, amido, nitro, amino, carboxy or $C_{1-4}$alkoxyy-carbonyl), 1-naphthylsulfinyl, 2-naphthylsulfinyl or substituted naphthylsulfinyl (where the naphthyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl);

a D or L amino acid which is coupled as its carboxy terminus to the nitrogen depicted in formula I and is selected from the group consisting of alanine, asparagine, 2-azetidinecarboxylic acid, glycine, N-$C_{1-8}$alkyglycine, proline, 1-amino-1-cyclo$C_{3-8}$alkylcarboxylic acid, thiazzolidine-4-carboxylic acid, 5,5-dimethylthiazolidine-4-carboxylic acid, oxadolidine-4-carboxylic acid, pipecolinic acid, valine, methionine, cysteine, serine, threonine, norleucine, leucine, tert-leucine, isoleucine, phenylalanine, 1-naphthalanine, 2-naphthalamine, 2-thienylalanine, 3-thienylalanine, [1,2,3,4]-tetrahydroisoquinoline-1-carboxylic acid and 1,2,3,4,]-tetrahydroisoquinoline-2-caroboxylic acid where the amino terminus of said amino acid is connected to a member selected form the group consisting of $C_{1-4}$alkyl,tetrazol-5yl-$C_{1-2}$alkyl, carboxyt$C_{1-4}$alkyl, $C_{1-4}$alkoxycarbonylC14alkyl, phenyl$C_{1-4}$alkyl, substituted phenyl $C_{1-4}$ allyl (where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboy or $C_{1-4}$alkoxycarbonyl), 1,1-diphenyl$C_{1-4}$alkyl, 3-phenyl-2-hydroxypropionyl, 2,2-diphenyl-1-hydroxyethylcarbonyl, [1,2,3,4]-tetrahydroisoquinoline-1-carbonyl, [1,2,3,4]-tetrahydroisoquinoline-3,carbonyl, 1-methylamino-1-cyclohexanecarbonyl, 1-hydroxy-1- cyclohexanecarbonyl, 1-hydroxy-1-pheny-lacetyl, 1-cyclohexyl-1-hydroxyacetyl, 3-phenyl-2-hydroxypropionyl, 3,3-diphenyl-2-hydroxypropionyl, 3-cyclohexyl-2-hydroxypropionyl, formyl, $C_{1-4}$alkoxycarbonyl, $C_{1-12}$alkylcarbonyl, perfluoro$C_{1-4}$alkyl, $C_{1-4}$alkylcarbonyl, phenyl$C_{1-4}$alkylcarbon1, substituted phenyl$C_{1-4}$alkylcarbonyl (where the phenyl substituents are independently selected from one or more of, $C_{1-4}$alkyl, perfluoro$C_{1-4}$alkyl, $C_{1-4}$alkoxy, hydroxy, halo amido, nitro amino, $C_{1-4}$alkylamino, $C_{1-4}$dialkylamino, carboxy or $C_{1-4}$alkoxycarbonyl) 1,1-diphenyl$C_{1-4}$alkylcarbonyl, substituted 1,1-diphenyl$C_{1-4}$alkylcarbonyl (where the phenyl substituents are independently selected from one or more of, $C_{1-4}$alkyl, perfluoro $C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxy-carbonyl), perfluoro$C_{1-4}$alkysulfonyl, $C_{1-4}$alkysulfonyl, $C_{1-4}$alkoxysulfonyl, phensulfonyl, substituted phenylsulfonyl (where the phenyl substituents are independently selected from one or more of, C-1alkyl, perfluoro $C_{1-4}$alkylamino, $C_{1-4}$dialkylamino, carboxy or $C_{1-4}$alkoxycarbonyl), 10-cxamphorsulfonyl, phenyl$C_{1-4}$alkylsulfonyl, substituted phenyl$C_{1-4}$alkylsufonyl, perfluro$C_{1-4}$alkysulfinyl, $C_{1-4}$alkysulfinyl, phenylsulfinyl, substituted phenysulfinyl (where the phenyl substituents are independently selected from one or more of, $C_{1-4}$alkyl, perfluoro $C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$ alkoxycarbonyl), 1-naphthysulfon 1, 2-naphthylsulfonyl, substituted naphthylsulfonyl (where the naphthyl substituents are independently selected from one or more of, $C_{1-4}$alkyl, perfluro$C_{1-4}$alkyl, $C_{1-4}$alkoxy, hydroxy, halo, amido, nitro, amino, $C_{1-4}$alkylamino, $C_{1-4}$dialkylamino, carboy or $C_{1-4}$alkoxycarbonyl),1-naphthysulfinyl, 2-naphthysulfinyl, and substituted naphthylsulfinyl (where the naphthyl substituents are independently selected from one or more of, $C_{1-4}$alkyl, perfluoro$C_{1-4}$alkyl, $C_{1-4}$alkoxy, hydroxy, halo amido, nitro, amino, $C_{1-4}$alkylamino, C104dialkylamono, carboxy or C-14alkoxycarbonyl):

or a poly peptide comprised of two amino acids,
  where the first amino acid is a D or L amino acid, bound via its carboxy terminus tot he nitrogen depicted in Formula I and is selected from the group consisting of glycine, N-$C_{1-8}$alkyglycine, alanine, 2-azetidinecarboxylic acid, proline, thiazolidine-4-carboxylic acid, 5.5-dimethylthiazolidine-4-carboxylic acid, oxazolidine-4-carboxylic acid, 1-amino-1-cyclo$C_{3-8}$ alkylcarboxylic acid, 3-hydroxypropoline, 4-hydroxyproline, 3-($C_{1-4}$alkoxy)proline, 4($C_{1-4}$alkoxy)proline, 3,4-dehydroprline, 2,2-dimethyl-4-thiazolidine carboxylic acid, 2.2-dimethyl-4-oxadolidine carboxylic acid, pipecolinic acid, valine, methionine, cysteine, asparagine, serine, threonine, leucine, tert-leucine, isoleucine, phenylalanine, 1-naphthalanine, 2-naphthalanine, 2-thienylalanine, 3-thienylalnine, [1,2,3,4]-tetrahydroisoquinoline-2-carboxylic acid, aspartic acid-4-$C_{1-4}$alkyl ester and glutamic acid 5-$C_{1-4}$alkyl ester and the second D or L amino acid, is bound to the amino terminus of said first amino acid, and is selected from the group consisting of phenylalanine, 4-benzolyphenylalanine, 4-carboxyphenylalanine, 4-(Carboxy C1-2alkyl) phenylalanine, substituted phenylalanine (where the phenyl substituents are independently selected from one or more of $C_{1-4}$alkyl, perfluoro$C_{1-4}$alkyl,$C_{1-4}$alkoxy, hydroxy, halo, amido, nitro, amino, $C_{1-4}$alkylamino, $C_{1-4}$dialkylamino, carboxy or $C_{1-4}$alkoxycarbonyl), 3-benzothienylalanine, 4-biphenylalanine, homophenylalanine, octahydroindole-2-carboxylic acid, 2-pyridylalanine, 3-pyridylalanine, 4-thiazolyalanine, 2-thienylalanie, 3-(3-benzothienyl) alanine, 3-thienylalanine, tryptophan, tyrosine, asparagine, 3-tri-$C_{1-4}$alkylsilysalanine, cyclohexylglycine, diphenylglycine, phenylglycine, methionine sulfoxide, methionine sulfone, 2,2-dicyclohexylalanine, 2-(1-naphthylalanine), 2-(2-naphthylalanine), phenyl substituted phenylalanine (where the substituents are selected from $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), aspartic acid, aspartic acid-4$C_{1-4}$alkyl, perfluoroc$_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbony), aspartic acid, aspartic acid-4-$C_{1-4}$alkyl ester glutamic acid, glutamic acid-5-$C_{1-4}$alkyl ester, cycloC3-salkylaalanine, substituted cyclo$C_{3-8}$alkylalanine (where the ring substituents are carboxy, $C_{1-4}$alkyl ester, cycloC3-salkylalanine, substituted cyclo$C_{3-8}$alkylalanine (where the ring substituents are carboxy, $C_{1-4}$alkylcarboxy, $C_{1-4}$alkoxycarbonyl or aminocarbonyl), 2,2-diphenylalanine and all alpha-$C_{1-5}$alkyl of all amino acid derivatives thereof, where the amino terminus of said second amino acid is unsubstituted or monosubstituted with a member of the group consisting of formyl, C1-12 alkyl, tetrazol-5-ylC1-2alkyl, carboxyC1-8 alkyl, carboalkoxy$C_{1-4}$alkyl, phenyl $C_{1-4}$alkyl, substituted phenyl$C_{1-4}$alkyl (where the phenyl substituents or independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), 1,1-dipehnyl$C_{1-4}$alkyl, C1-6alkoxycarbonyl, phenylC1-6alkoxycarbonyl, C1-2alkylcarbonyl, perfluoro$C_{1-4}$alkylCo-4alkylcarbonyl, pheny$C_{1-4}$alkylcarbonyl, substituted pheny$C_{1-4}$alkylcarbonyl(where the phenyl substituents are independently selected from one or more of $C_{1-4}$alkyl, perfluoro $C_{1-4}$alkyl, $C_{1-4}$alkoxy, hydroxy, halo, anido, nitro, amino, $C_{1-4}$alkylamino, $C_{1-4}$dialkylamino, carboxy or $C_{1-4}$alkoxycarbonyl), 1,1-diphenyl$C_{1-4}$alkyl, perfluoro$C_{1-4}$alkyl, $C_{1-4}$alkoxycarbonyl), 10-camphorsulfonyl, phenyl$C_{1-4}$alkysulfonyl, substituted phenyl$C_{1-4}$alkylsulfonyl, $C_{1-4}$alkysulfinyl, perfluoro $C_{1-4}$alkysulfinyl, phenylsulfinyl, substituted phenylsulfinyl (where the phenyl substituents are independently selected from one or more of, $C_{1-4}$alkyl perfluoro$C_{1-4}$alkyl, $C_{1-4}$alkoxy, hydroxy, halo, amido, nitro, amino, $C_{1-4}$alkylamono, $C_{1-4}$dialkylamono, carboxy or $C_{1-4}$alkoxycarbonyl), pheny$C_{1-4}$alkylsulfinyl, substituted phenyl$C_{1-4}$alkylsulfinyl 1-naphthylsulfonyl, 2-naphthylsulfonyl, substituted naphthylsulfonyl (where the naphthyl substituent is selected from $C_{1-4}$alkyl, perfluoro $C_{1-4}$alkyl, $C_{1-4}$alkoxy, hydroxy, halo amido, nitro, amino, $C_{1-4}$alkylamino, $C_{1-4}$dialkylamino, carboxy or $C_{1-4}$alkoxycarbonyl), 1-haphthyl-sulfinyl, 2-haphthylsulfinyl and substituted naphthyl-sulfinyl (where the naphthyl substituent is selected from $C_{1-4}$alkyl, perfluoro$C_{1-4}$alkyl, $C_{1-4}$alkoxy, hydroxy, halo, amido, nitro, amino, $C_{1-4}$alkylamino, C-14dialkylamino, carboxy or $C_{1-4}$alkoxycarbonyl); $R_1$ is selected from the group consisting of hydrogen and alkyl; $R_2$ is selected from the group consisting of aminoC2-salkyl, guanidino$C_{2-5}$alkyl, $C_{1-4}$alkylguanidino$C_{2-5}$alkyl,di$C_{1-4}$alkylguanidino $C_{2-5}$alkyl, amidino$C_{2-5}$alkyl, $C_{1-4}$alky-lamidino$C_{2-5}$alkyl, diC$_{1-4}$alky-lamidinoC$_{2-5}$alkyl, C$_{1-3}$alkoxyC$_{2-5}$alkyl, phenyl, substituted phenyl (where the substituents are independently selected from one or more of amino, amidino, guanidino, C$_{1-4}$alkylamino, C$_{1-4}$dialkylamino, halogen, perfluoro C$_{1-4}$alkyl, C$_{1-4}$alkyl, C$_{1-3}$ alkoxy or nitro), benzyl, phenyl substituted benzyl (where the substituents are independently selected from one or more of, amino, amidino, guanidino, C$_{1-4}$alkylamino, C$_{1-4}$dialky-lamino, halogen, perfluoro C$_{1-4}$alkyl, C1-04alkyl, C$_{1-3}$alkoxy or nitro), hydroxyC$_{2-5}$alkl, C$_{1-5}$alkylaminoC$_{2-5}$alky, C$_{1-5}$dialkylaminoC$_{2-5}$alkyl, 4-aminocyclohexylC$_{0-2}$alkyl and C$_{1-5}$alkyl;

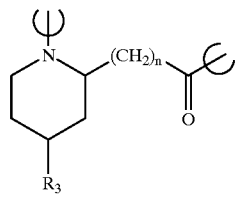

where n is 0–3, R$_3$ is H or C1-5alkyl and the carbonyl moiety of B is bound to E; E is a heterocycle selected from the group consisting of oxazolin-2-yl, oxazol-2-yl, thiazol-2-yl, thiazol-5-yl, thiazol-4-yl, thiazolin-2-yl, imidazol-2-yl, 4-oxo-2-quinoxalin-2yl, 2-pyridyl, 3-pyridyl, benzo[b}thiophen-2-yl, triazol-4-yltriazol-6-yl, pyrazol-2-yl, 4,5,6,7-tetrahydrobenzothiazol-2yl, naphtho[2,1-d]tyhiazol-2-yl, naphtho[1-2-d]thiazol-2-yl quinoxalin- 2-yl, isoquinolin-1-yl, isoquinolin-3-yl, benzo [b]furan-2-yl [pyrazin-2-yl, quinazolin-2-yl, isothiazol-5-yl, isothiazol-3-yl, purin-8yul and a substituted heterocycle where the substituents are selected from C$_{1-4}$ from C-14alky, perfluoro C$_{1-4}$alkyl,C$_{1-4}$alkoxy, hydroxy, halo, amido, nitro, amino, C$_{1-4}$alkylamino, C$_{1-4}$dialkylamino, carboxy, C$_{1-4}$alkoxycarbonyl, hydroxy or phenylC$_{1-4}$ alkylaminocarbonyl;

or pharmaceutically acceptable salts thereof.

More particularly, in our opinion, some of the compounds of the foregoing formula containing a d-phenylalanine-proline-arginine motif should be effective in inhibiting the PAR-2 pathway and causing depigmentation. One particularly preferred compound which acts as a thrombin and trypsin inhibitor and is active in depigmenting mammalian skin is (S)-N-Methyl-D-phenylalanyl-N-[4[(aminoiminomethyl)amino]-1-(2-benzothiazolylcarbonyl)butyl]-L-prolinamide (Chemical Abstracts name) (hereinafter referred to as "Compound I"). We suggest that other compounds which are analogs or function similarly to Compound I and are set forth in U.S. Pat. No. 5,523,308 may be active in the methods and compositions of this invention.

Other compounds that inhibit trypsin, such as serine protease inhibitors, and in particular, soybean trypsin inhibitor (STI) will also be useful in methods of this invention. Soybean, limabean and blackbean extracts, and other natural products made from these beans, such as, but not limited to, bean milk, bean paste, miso and the like, also serve to reduce pigmentation by this mechanism.

Additional sources of serine protease inhibitors may be extracted from the species belonging to the following plant families: Solanaceae (e.g., potato, tomato, tomatilla, and the like); Gramineae (e.g., rice, buckwheat, sorghum, wheat, barley, oats and the like); Cucurbitaceae (e.g., cucumbers, squash, gourd, luffa and the like); and, preferably, Leguminosae (e.g., beans, peas, lentils, peanuts, and the like).

While not willing to be bound by the following theory, we theorize that the compounds capable of affecting the pigmentation of the skin do so by interacting directly or indirectly with the keratinocyte PAR-2 or with its activating protease, and thereby affect melanogenesis, directly or indirectly. Possibly, the compounds of this invention induce, in the case of increased pigmentation or reduce, in the case of decreased pigmentation, the signal to transport melanosomes by melanocytes, or to receive melanosomes by keratinocytes in the skin.

Recently we have identified that the Bowman-Birk Inhibitor ("BBI"), a different group of legume-derived proteins, are also depigmenting agents.

While STI is a 21 KD protein with primarily trypsin inhibitory activity, the soybean-derived BBI is a smaller, 8 KD protein, which inhibits chymotrypsin and trypsin. Unlike STI, BBI does not have a Kunitz-type domain, suggesting different interactions with serine proteases. BBI is known for its ability to prevent carcinogenesis in numerous in vivo and in vitro models. In some animal carcinogenesis models BBI was found to have strong anti-inflammatory effects. BBI is more resistant than STI to heat-denaturation. For a review on BBI see Kennedy AR, Chemopreventive agents: protease inhibitors, Pharmacol Ther 78: 3, 167–209, June 1998.

The compounds which are active in the compositions and methods of this invention may be delivered topically by any means known to those of skill in the art. If the delivery parameters of the topically active pharmaceutical or cosmetic agent so require, the topically active composition of this invention may preferably be further composed of a pharmaceutically or cosmetically acceptable vehicle capable of functioning as a delivery system to enable the penetration of the topically active agent into the skin.

One acceptable vehicle for topical delivery of some of the compositions of this invention, particularly proteins such as trypsin and STI, may contain liposomes. The liposomes are more preferably non-ionic and contain a) glycerol dilaurate (preferably in an amount of between about 5% and about 70% by weight); b) compounds having the steroid backbone found in cholesterol (preferably in an amount of between about 5% and about 45% by weight); and c) one or more fatty acid ethers having from about 12 to about 18 carbon atoms preferably in an amount of between about 5% and about 70% by weight collectively), wherein the constituent compounds of the liposomes are preferably in a ratio of about 37.5:12.5:33.3:16.7. Liposomes comprised of glycerol dilaurate/cholesterol/polyoxyethylene -10-stearyl ether/polyoxyethylene-9-lauryl ether (GDL liposomes) are most preferred. Preferably the liposomes are present in an amount, based upon the total volume of the composition, of from about 10 mg/mL to about 100 mg/mL, and more preferably from about 20 mg/mL to about 50 mg/mL. A ratio of about 37.5:12.5:33.3:16.7 is most preferred. Suitable liposomes may preferably be prepared in accordance with the protocol set forth in Example 1, though other methods commonly used in the art are also acceptable.

The above described composition may be prepared by combining the desired components in a suitable container and mixing them under ambient conditions in any conventional high shear mixing means well known in the art for non-ionic liposomes preparations, such as those disclosed in Niemiec et al., "Influence of Nonionic Liposomal Composition On Topical Delivery of Peptide Drugs Into Pilosebacious Units: An In Vivo Study Using the Hamster Ear Model," 12 Pharm. Res. 1184–88 (1995) ("Niemiec"), which is incorporated by reference herein in its entirety. We have found that the presence of these liposomes in the compositions of this invention may enhance the depigmenting capabilities of some of the compositions of this invention.

Other preferable formulations may contain, for example, soybean milk or other liquid formulations derived directly from legumes or other suitable plant. For example, such a formulation may contain a large proportion of soybean milk, an emulsifier that maintains the physical stability of the soybean milk, and, optionally a chelating agent, preservatives, emollients, humectants and/or thickeners or gelling agents.

Oil-in-water emulsions, water-in-oil emulsions, solvent-based formulations and aqueous gels known to those of skill in the art may also be utilized as vehicles for the delivery of the compositions of this invention.

The source of active compound to be formulated will generally depend upon the particular form of the compound. Small organic molecules and peptidyl fragments can be chemically synthesized and provided in a pure form suitable for pharmaceutical/cosmetic usage. Products of natural extracts can be purified according to techniques known in the art. Recombinant sources of compounds are also available to those of ordinary skill in the art.

In alternative embodiments, the topically active pharmaceutical or cosmetic composition may be optionally combined with other ingredients such as moisturizers, cosmetic adjuvants, anti-oxidants, bleaching agents, tyrosinase inhibitors and other known depigmentation agents, surfactants, foaming agents, conditioners, humectants, fragrances, viscosifiers, buffering agents, preservatives, sunscreens and the like. The compositions of this invention may also contain active amounts of retinoids (i.e., compounds that bind to any members of the family of retinoid receptors), including, for example, tretinoin, retinol, esters of tretinoin and/or retinol and the like.

The topically active pharmaceutical or cosmetic composition should be applied in an amount effective to affect changes in the pigmentation of mammalian skin. As used herein "amount effective" shall mean an amount sufficient to cover the region of skin surface where a change in pigmentation is desired. Preferably, the composition is liberally applied to the skin surface such that, based upon a square cm of skin surface, from about 2 $\mu l/cm^2$ to about 200 $\mu l/cm^2$ of topically active agent is present when a change in pigmentation is desired. When using a thrombin and trypsin inhibitor such as Compound I or its analogs, whether synthetically- or naturally-derived in a formulation, such an active compound should be present in the amount of from about 0.0001% to about 15% by weight/volume of the composition. More preferably, it should be present in an amount from about 0.0005% to about 5% of the composition; most preferably, it should be present in an amount of from about 0.001 to about 1% of the composition. Of course, these ranges are suggested for the foregoing components. The lower set of ranges is intended to be efficacious for PAR-2 pathway agonists/antagonists and/or inhibitors having high therapeutic indices and which do not require significantly larger concentrations or doses to be effective in the methods of this invention. Such compounds may be synthetically- or naturally-derived.

Liquid derivatives and natural extracts made directly from plants or botanical sources may be employed in the compositions of this invention in a concentration (w/v) from about 1 to about 99%. Fractions of natural extracts and naturally-derived protease inhibitors such as STI may have a different preferred range, from about 0.01% to about 20% and, more preferably, from about 1% to about 10% of the composition. Of course, mixtures of the active agents of this invention may be combined and used together in the same formulation, or in serial applications of different formulations.

We have unexpectedly found that when topically active agents, such as PAR-2 agonists and/or inhibitors and trypsin and/or thrombin and/or tryptase and/or their inhibitors, are topically applied to an animal's skin, a significant change in pigmentation was achieved. Preferably, depigmenting agents (as well as other pigmentation-affecting agents of this invention) are applied to the skin of a mammal at a relatively high concentration and dose (from about 0.005% to about 1% for compounds having high therapeutic indices such as Compound I and related compounds; from about 20% to about 99% for liquid derivatives and extracts of botanical materials; and from about 1% to about 20% for fractions of natural extracts and naturally-derived protease inhibitors such as STI or mixtures thereof) between one and two times daily for a period of time until the skin evidences a change in pigmentation. This may be for from about four to about ten weeks or more. Thereafter, once the change in pigmentation has been achieved, a lower concentration and dose (from about 0.00001% to about 0.005% for compounds having high therapeutic indices such as Compound I and related compounds; from about 10% to about 90% for liquid derivatives and extracts of botanical materials; and from about 0.01% to about 5% for fractions of natural extracts and naturally-derived protease inhibitors such as STI or mixtures thereof), of active ingredient may be applied on a less frequent time schedule, e.g., about once per day to about twice per week. The effects of the active agents of this invention are reversible, therefore, in order to maintain these effects, continuous application or administration should be performed. The invention illustratively disclosed herein suitably may be practiced in the absence of any component, ingredient, or step which is not specifically disclosed herein.

The invention illustratively disclosed herein suitably may be practiced in the absence of any component, ingredient, or step which is not specifically disclosed herein. Several examples are set forth below to further illustrate the nature of the invention and the manner of carrying it out, but do not serve to limit the scope of the methods and compositions of this invention.

EXAMPLE 1

BBI Affects Pigmentation

In order to study the possible roles of BBI in pigmentation, an in vitro epidermal equivalent system containing melanocytes was used. The epidermal equivalent system used in this study is the MelanoDerm mel-300 system, available commercially from MatTek Co. of Ashland, Mass. This system contains human normal melanocytes, together with normal, human-derived epidermal keratinocytes, derived from African-American foreskin. These cells have been cultured to form a multi-layered, highly differentiated model of the human epidermis. In do the following examples, equivalents were treated with BBI (0.1%) for three days and samples were harvested on the fourth day after beginning of treatment. The harvested equivalents were first compared for their color without staining, following by histological examination with Fontana-Mason F&M staining, a stain known to those of skill in the art. F&M staining is a silver staining technique that clearly and cleanly marks melanins which have high silver nitrate reducing activity. Images of the stained sections were also captured for image analysis. At least three sections per equivalent, three equivalents per experiment were processed. Empire Images database 1.1 was used on a Gateway 2000 P5-100 computer Media Cybernetics, Silver Springs, Md.) for capturing images. Image Pro Plus version 3.0 was used for image analysis. Parameters measured were the surface area of silver deposits within melanocytes and the density luminosity of each pixel. A "pigmentation factor" was defined as the surface area of silver deposits divided by the total epidermal surface area. A value of one (100%) was assigned to untreated controls, and values of treatment groups were normalized to their relevant controls.

Figure 2:
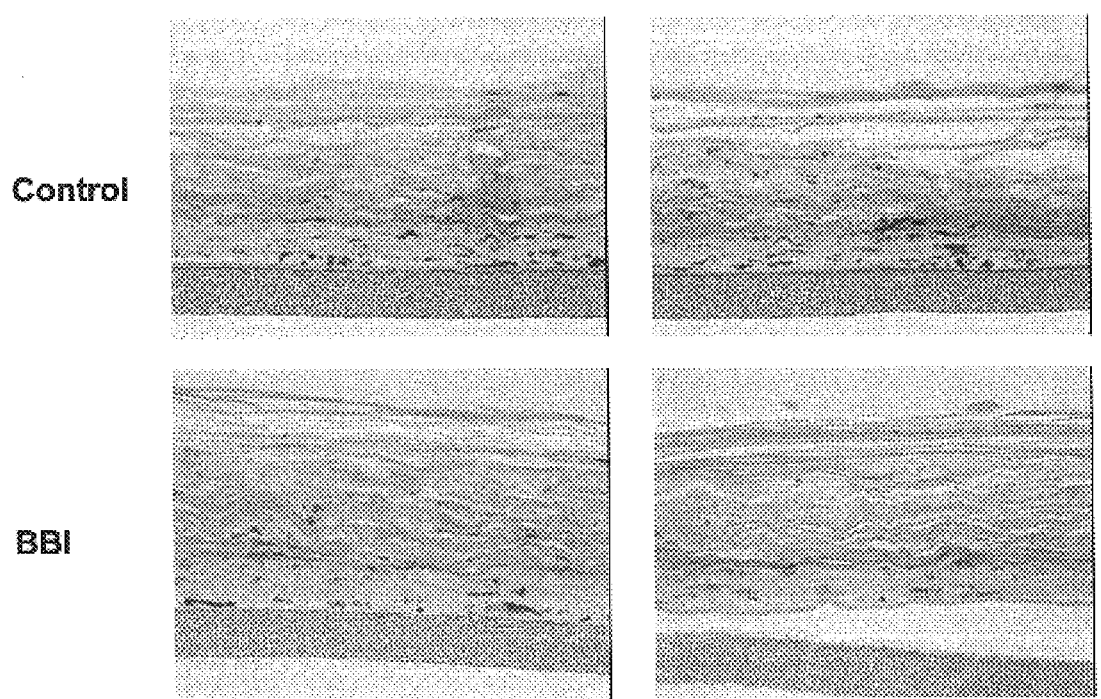
FIG. 2 shows epidermal equivalents containing melanocytes of an African-American donor. Treatment with BBI reduces pigment deposition in these equivalents, as demonstrated by Fontana-Mason staining of histological sections of these equivalents.

As shown in FIG. 1, untreated mel-300 equivalents are visibly dark without any staining. BBI treated equivalents were lighter than these controls, demonstrating the ability of BBI to visually reduce pigmentation. FIG. 2 shows the histological sections of these equivalents, following F&M staining. In this Figure, black areas represent melanin deposits within both melanocytes and keratinocytes. As shown in FIG. 2, BBI treatment results in reduced melanin deposition both in the melanocytes and in the keratinocytes of the treated equivalents. Image analysis revealed that BBI treated equivalents have only 50.6% melanin deposits relative to controls.

EXAMPLE 2

The Depigmenting Effect of BBI is Dose-responsive

Figure 3:
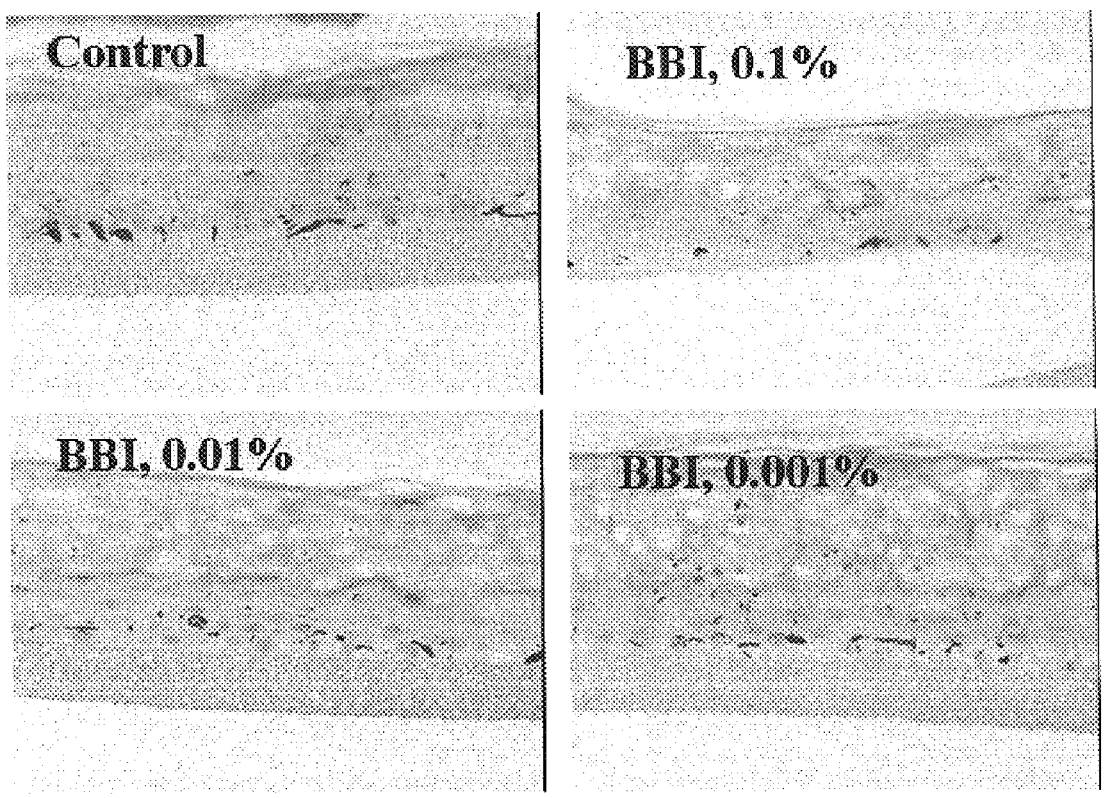
FIG. 3 shows epidermal equivalents containing melanocytes of an African-American donor. Treatment with increasing concentrations of BBI reduces pigment deposition in these equivalents in a dose-dependent fashion, as demonstrated by Fontana-Mason staining of histological sections of these equivalents.
Figure 4:
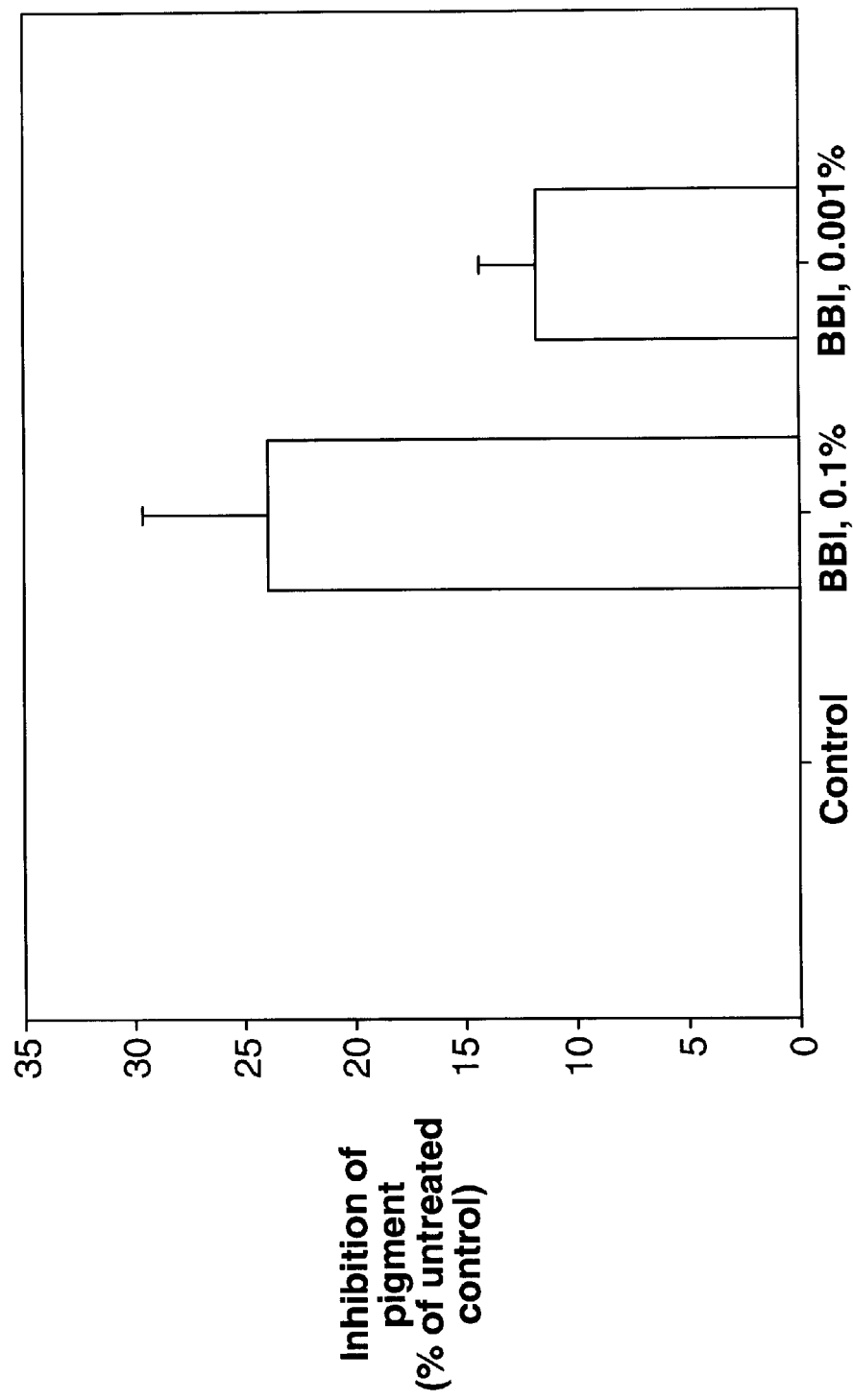
FIG. 4 is a graph quantifying the percent of inhibition of pigment deposition following BBI treatment.

Epidermal equivalents containing melanocytes as described in example 1 were treated with increasing concentrations of BBI, from 0.001% to 0.1%. Following the same experimental procedure described in example 1, the depigmenting effect of BBI was found to be dose-dependent. FIG. 3 shows F&M stained sections of the treated equivalents, demonstrating the dose-response and the depigmenting effect of as low as 0.001% BBI. Computerized image analysis, shown in FIG. 4, quantifies this effect and further demonstrates its dose-responsive nature.

EXAMPLE 3

In Vivo Demonstration of the Depigmenting Effect of BBI

A dark skin Yucatan microswine was treated with BBI, or STI, 1%, in PBS, with 20/mg/ml liposomes. Non-ionic liposomes preparations, such as those disclosed in Niemiec et al., "Influence of Nonionic Liposomal Composition On Topical Delivery of Peptide Drugs Into Pilosebacious Units: An In Vivo Study Using the Hamster Ear Model," 12 Pharm. Res. 1184–88 (1995) ("Niemiec"), which is incorporated by reference herein in its entirety, are well known in the art, and are described in JBP430. We have found that the presence of these liposomes in the compositions of this invention may enhance the depigmenting capabilities of some of the compositions of this invention. GDL liposomes were prepared as set forth in Niemiec, et al., above, with the exception of the following changes: the non-ionic liposomal formulation contained glycerol dilaurate (Emulsynt GDL, ISP Van Dyk)/cholesterol (Croda)/polyoxyethylene-10-stearyl ether (Brij76, ICI)/polyoxyethylene-9-laurylether, as at ratio of 37.5:12.5:33.3:16.7. Hepes buffer, 0.05M, pH 7.4 (Gibco-BRL of Gaithersburg, Md.) was used as the aqueous phase in the preparation of the liposomes.

Figure 5:
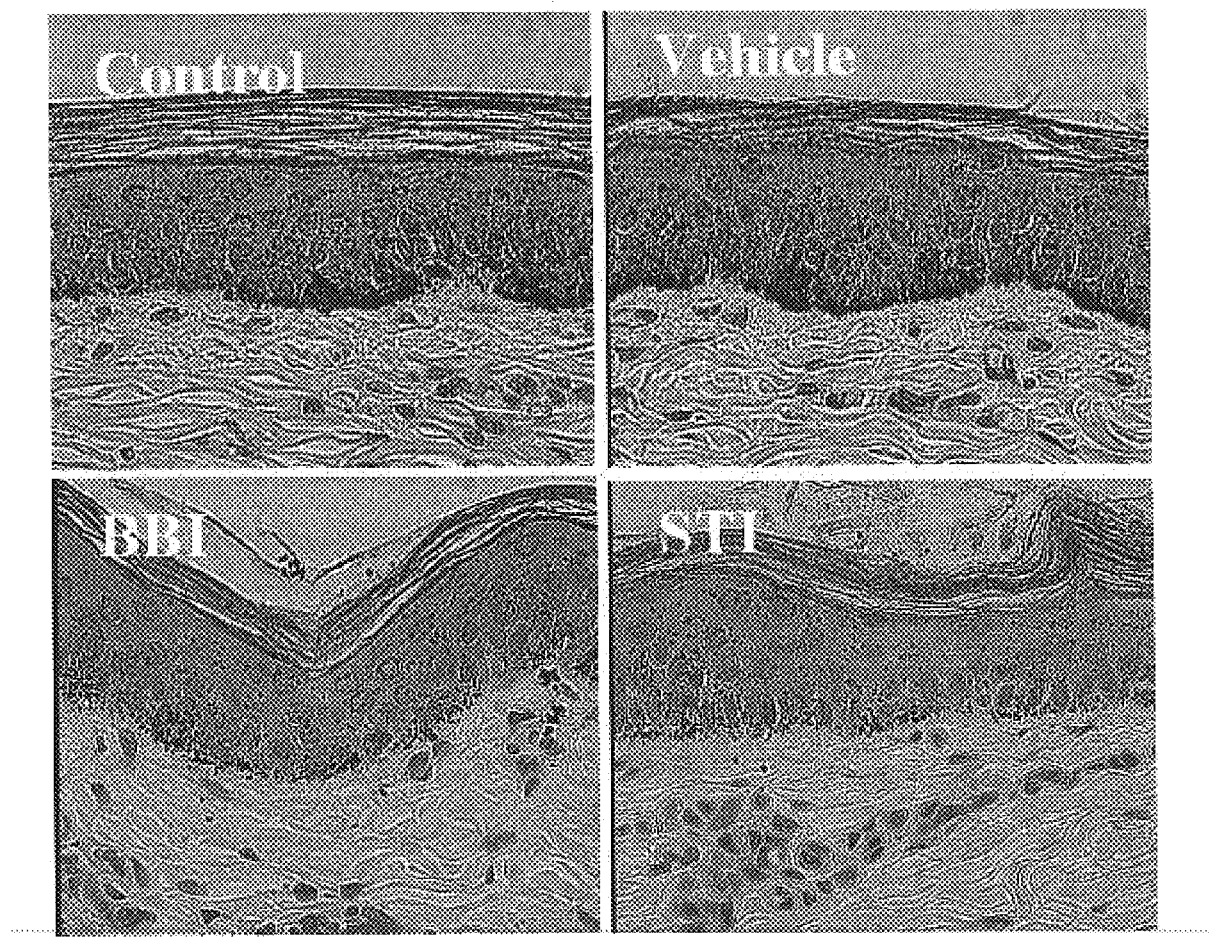
FIG. 5 shows F&M stained histological sections from swine skin treated with BBI and STI. Melanin deposition in the swine skin is dramatically reduced following BBI or STI treatment.

The BBI, STI and liposome vehicle preparations were applied each onto two sites of the swine's flank, twice daily, five days per week, for eight weeks. After eight weeks of treatment, the application of either BBI or STI resulted in a visible lightening effect. Histological analysis of F&M stained skin sections from untreated and treated sites confirmed this observation. FIG. 5 shows the F&M stained skin sections of the treated swine, demonstrating a dramatic reduction in pigment deposition in sites treated with BBI or STI. Computerized image analysis, shown in FIG. 6, quantifies this effect and further demonstrates the depigmenting effect of BBI.

What is claimed is:

1. A method of effecting changes in mammalian skin pigmentation comprising administering to a mammal a pigmentation-changing effective amount of a Bowman-Birk Inhibitor or of a natural extract containing a Bowman-Birk Inhibitor.

2. A method of depigmenting mammalian skin pigmentation comprising administering to a mammal a pigmentation-lightening effective amount of a Bowman-Birk Inhibitor or of a natural extract containing a Bowman-Birk Inhibitor.

3. A method according to claim 2 wherein said Bowman-Birk Inhibitor is derived from one or more of the botanical families leguminosae, solanaceae, gramineae and cucurbitaceae.

4. A method according to claim 3 wherein said compound is derived from legumes.

5. A method according to claim 4 wherein said compound is derived from undenatured soybean extract.

6. A method according to claim 5 wherein said compound is derived from fractions of undenatured soybean extract.

7. A method according to claim 1 wherein said composition is applied at least once daily for at least eight weeks.

8. A method according to claim 7 wherein said composition is applied at a relatively high dosage for at least about four to about ten weeks and then applied at a relatively lower dosage on a continuous basis to maintain skin lightening effect.

9. A method of effecting changes in mammalian pigmentation comprising administering orally a pigmentation-changing effective amount of a Bowman-Birk Inhibitor or of a natural extract containing a Bowman-Birk Inhibitor.

10. A method of effecting changes in mammalian pigmentation comprising administering parenterally a pigmentation-changing effective amount of a Bowman-Birk Inhibitor or of a natural extract containing a Bowman-Birk Inhibitor.

* * * * *